US012605394B2

(12) United States Patent
Tremblay

(10) Patent No.: US 12,605,394 B2
(45) Date of Patent: Apr. 21, 2026

(54) COMPOSITIONS CONTAINING CANNABINOID NANOPARTICLES

(71) Applicant: Mario Tremblay, St. Petersburg, FL (US)

(72) Inventor: Mario Tremblay, St. Petersburg, FL (US)

(73) Assignee: VISIONARY ASSETS, LLC, Troy, MI (US)

( * ) Notice: Subject to any disclaimer, the term of this patent is extended or adjusted under 35 U.S.C. 154(b) by 167 days.

(21) Appl. No.: 18/783,428

(22) Filed: Jul. 25, 2024

(65) Prior Publication Data

US 2026/0027134 A1     Jan. 29, 2026

(51) Int. Cl.
| | |
|---|---|
| *A61K 9/14* | (2006.01) |
| *A61K 9/00* | (2006.01) |
| *A61K 31/00* | (2006.01) |
| *A61K 31/145* | (2006.01) |
| *A61K 31/194* | (2006.01) |
| *A61K 31/197* | (2006.01) |
| *A61K 31/198* | (2006.01) |
| *A61K 31/355* | (2006.01) |
| *A61K 31/365* | (2006.01) |
| *A61K 31/375* | (2006.01) |
| *A61K 31/4415* | (2006.01) |
| *A61K 31/455* | (2006.01) |
| *A61K 31/522* | (2006.01) |
| *A61K 31/593* | (2006.01) |
| *A61K 31/714* | (2006.01) |
| *A61K 33/00* | (2006.01) |
| *A61K 33/04* | (2006.01) |
| *A61K 33/06* | (2006.01) |
| *A61K 33/30* | (2006.01) |
| *A61K 33/32* | (2006.01) |
| *A61K 33/34* | (2006.01) |
| *A61K 36/185* | (2006.01) |

(52) U.S. Cl.
CPC .......... *A61K 31/658* (2023.05); *A61K 9/0095* (2013.01); *A61K 9/14* (2013.01); *A61K 31/145* (2013.01); *A61K 31/194* (2013.01); *A61K 31/197* (2013.01); *A61K 31/198* (2013.01); *A61K 31/355* (2013.01); *A61K 31/365* (2013.01); *A61K 31/375* (2013.01); *A61K 31/4415* (2013.01); *A61K 31/455* (2013.01); *A61K 31/522* (2013.01); *A61K 31/593* (2013.01); *A61K 31/714* (2013.01); *A61K 33/00* (2013.01); *A61K 33/04* (2013.01); *A61K 33/06* (2013.01); *A61K 33/30* (2013.01); *A61K 33/32* (2013.01); *A61K 33/34* (2013.01); *A61K 36/3482* (2024.05)

(58) Field of Classification Search
None
See application file for complete search history.

(56) References Cited

U.S. PATENT DOCUMENTS

| | | | |
|---|---|---|---|
| 7,649,002 B2 | 1/2010 | Calabrese et al. |
| 8,102,347 B2 | 1/2012 | Yoshida et al. |
| 8,138,188 B2 | 3/2012 | Andrews et al. |
| 8,258,137 B2 | 9/2012 | Augustijns et al. |
| 8,349,353 B2 | 1/2013 | Lichter et al. |

(Continued)

*Primary Examiner* — Ernst V Arnold
(74) *Attorney, Agent, or Firm* — JUNEAU & MITCHELL; Todd L. Juneau

(57) ABSTRACT

The invention relates generally to beverage compositions comprising cryogenically produced cannabinoid nanoparticles using cannabinoids made from hemp, and processes for making the same.

29 Claims, 19 Drawing Sheets

(56)  References Cited

U.S. PATENT DOCUMENTS

| | | | |
|---|---|---|---|
| 8,399,018 B2 | 3/2013 | Lichter et al. |
| 8,642,080 B2 | 2/2014 | Bender et al. |
| 8,648,119 B2 | 2/2014 | Lichter et al. |
| 8,709,385 B2 | 4/2014 | Tamarkin et al. |
| 8,765,744 B2 | 7/2014 | Himmelsbach |
| 9,006,197 B2 | 4/2015 | Bumcrot et al. |
| 9,066,855 B2 | 6/2015 | Lichter et al. |
| 9,458,199 B2 | 10/2016 | Frost et al. |
| 9,499,543 B2 | 11/2016 | Sudo et al. |
| 9,549,901 B2 | 1/2017 | Shi et al. |
| 9,580,727 B1 | 2/2017 | Donohoue et al. |
| 9,644,215 B2 | 5/2017 | Brenner et al. |
| 9,687,027 B2 | 6/2017 | Poston et al. |
| 9,783,576 B2 | 10/2017 | Fukuda et al. |
| 10,022,436 B2 | 7/2018 | Henderson |
| 10,096,033 B2 | 10/2018 | Heath |
| 10,125,375 B2 | 11/2018 | Van Der Oost et al. |
| 10,179,779 B2 | 1/2019 | Numata et al. |
| 10,232,044 B2 | 3/2019 | Lichter et al. |
| 10,265,380 B2 | 4/2019 | Schwartz et al. |
| 10,350,581 B2 | 7/2019 | Nagao et al. |
| 10,383,858 B2 | 8/2019 | Konstantinova et al. |
| 10,414,771 B2 | 9/2019 | Fatatis et al. |
| 10,653,820 B2 | 5/2020 | Taylor et al. |
| 10,680,300 B2 | 6/2020 | Mitlin et al. |
| 10,701,962 B2 | 7/2020 | Chen |
| 10,772,828 B2 | 9/2020 | Lichter et al. |
| 10,845,367 B2 | 11/2020 | Mileni et al. |
| 11,123,365 B2 | 9/2021 | Perricone |
| 11,254,773 B2 | 2/2022 | Helgeson et al. |
| 11,262,326 B2 | 3/2022 | Wang et al. |
| 11,517,685 B2 | 12/2022 | Danek |
| 11,703,471 B1 | 7/2023 | Gregory et al. |
| 11,739,085 B2 | 8/2023 | Cacatian et al. |
| 11,833,118 B2 | 12/2023 | Boeckl et al. |
| 11,849,741 B2 | 12/2023 | Ajami et al. |
| 11,883,165 B2 | 1/2024 | Rogers et al. |
| 11,883,557 B2 | 1/2024 | Reed et al. |
| 11,883,587 B2 | 1/2024 | Conner et al. |
| 12,011,535 B2 | 6/2024 | Danek et al. |
| 12,134,582 B2 | 11/2024 | Garnier et al. |
| 12,268,780 B1 | 4/2025 | Morrison |
| 12,274,690 B2 | 4/2025 | Miles |
| 12,280,145 B1 | 4/2025 | Morrison |
| 2002/0147232 A1 | 10/2002 | Sundgreen et al. |
| 2003/0094626 A1 | 5/2003 | Duggal et al. |
| 2004/0156792 A1 | 8/2004 | Tarara et al. |
| 2004/0260318 A1 | 12/2004 | Hunter et al. |
| 2005/0272784 A1 | 12/2005 | Li et al. |
| 2006/0246141 A1 | 11/2006 | Liversidge et al. |
| 2006/0293309 A1 | 12/2006 | Thor et al. |
| 2007/0072939 A1 | 3/2007 | Kupper |
| 2007/0252240 A1 | 11/2007 | Andresen et al. |
| 2008/0113031 A1 | 5/2008 | Moodley et al. |
| 2008/0213374 A1 | 9/2008 | Carty et al. |
| 2008/0253960 A1 | 10/2008 | Zheng et al. |
| 2008/0269233 A1 | 10/2008 | Andrews et al. |
| 2009/0005354 A1 | 1/2009 | Allerton et al. |
| 2009/0008608 A1 | 1/2009 | Bublitz et al. |
| 2009/0022823 A1 | 1/2009 | Ehrich et al. |
| 2009/0156563 A1 | 6/2009 | Baschong et al. |
| 2010/0226989 A1 | 9/2010 | Hovey et al. |
| 2010/0247606 A1 | 9/2010 | Robinson et al. |
| 2011/0293701 A1 | 12/2011 | Bratzler et al. |
| 2012/0131701 A1 | 5/2012 | Shekdar |
| 2012/0177701 A1 | 7/2012 | Ilyinskii et al. |
| 2013/0004542 A1 | 1/2013 | Martyn |
| 2013/0039954 A1 | 2/2013 | Pittet et al. |
| 2013/0122064 A1 | 5/2013 | Ahlheim et al. |
| 2013/0345286 A1 | 12/2013 | Gollob et al. |
| 2014/0079639 A1 | 3/2014 | McDaniel |
| 2014/0187583 A1 | 7/2014 | Numata et al. |
| 2014/0336243 A1 | 11/2014 | Bumcrot et al. |
| 2014/0343060 A1 | 11/2014 | Holland et al. |
| 2015/0030757 A1 | 1/2015 | McClain et al. |
| 2015/0104502 A1 | 4/2015 | Linder et al. |
| 2015/0110875 A1 | 4/2015 | Linder et al. |
| 2015/0306236 A1 | 10/2015 | Linder et al. |
| 2017/0073311 A1 | 3/2017 | Johnson et al. |
| 2017/0081318 A1 | 3/2017 | Numata et al. |
| 2017/0216439 A1 | 8/2017 | Lebel et al. |
| 2017/0367973 A1 | 12/2017 | Tonge et al. |
| 2018/0236016 A1 | 8/2018 | Gamay |
| 2018/0310599 A1 | 11/2018 | Ajami et al. |
| 2019/0080800 A1 | 3/2019 | Beim |
| 2019/0110981 A1 | 4/2019 | Weimann |
| 2019/0194320 A1 | 6/2019 | Orwar et al. |
| 2019/0216895 A1 | 7/2019 | Linder et al. |
| 2019/0254302 A1 | 8/2019 | Abbaspourrad et al. |
| 2019/0298799 A1 | 10/2019 | Lichter et al. |
| 2019/0314790 A1 | 10/2019 | Gao et al. |
| 2019/0330443 A1 | 10/2019 | Kander |
| 2019/0381137 A1 | 12/2019 | Linder et al. |
| 2020/0060349 A1 | 2/2020 | Danek |
| 2020/0093785 A1 | 3/2020 | Stauff |
| 2020/0120989 A1 | 4/2020 | Danek |
| 2020/0155469 A1 | 5/2020 | Small-Howard et al. |
| 2020/0155611 A1 | 5/2020 | Yadid et al. |
| 2020/0155642 A1 | 5/2020 | Lerer |
| 2020/0179908 A1 | 6/2020 | Simmance et al. |
| 2020/0215024 A1 | 7/2020 | Berman et al. |
| 2020/0238256 A1 | 7/2020 | Zurcher et al. |
| 2020/0345684 A1 | 11/2020 | Vialpando et al. |
| 2020/0353099 A1 | 11/2020 | Anderson et al. |
| 2020/0367961 A1 | 11/2020 | Podmore et al. |
| 2020/0376057 A1 | 12/2020 | Hansen et al. |
| 2020/0390881 A1 | 12/2020 | Lipford et al. |
| 2020/0405657 A1 | 12/2020 | Small-Howard et al. |
| 2021/0055050 A1 | 2/2021 | Triglia, Jr. |
| 2021/0106687 A1 | 4/2021 | Linder et al. |
| 2021/0128534 A1 | 5/2021 | Benita et al. |
| 2021/0186943 A1 | 6/2021 | Bishop et al. |
| 2021/0219550 A1 | 7/2021 | Van Rooijen et al. |
| 2021/0220263 A1 | 7/2021 | Lichter et al. |
| 2021/0220268 A1 | 7/2021 | Burnam |
| 2021/0228497 A1 | 7/2021 | Weimann |
| 2021/0251917 A1 | 8/2021 | Sloat et al. |
| 2021/0251946 A1 | 8/2021 | Gydosh |
| 2021/0254085 A1 | 8/2021 | Van Rooijen et al. |
| 2021/0290524 A1 | 9/2021 | Woolf et al. |
| 2021/0299081 A1 | 9/2021 | Yuan et al. |
| 2021/0379425 A1 | 12/2021 | Tran |
| 2021/0381023 A1 | 12/2021 | Tran |
| 2021/0393519 A1 | 12/2021 | Lucas et al. |
| 2021/0393540 A1 | 12/2021 | Lucas et al. |
| 2021/0401794 A1 | 12/2021 | Palaio |
| 2022/0008348 A1 | 1/2022 | Golfetto |
| 2022/0008349 A1 | 1/2022 | Paliyath et al. |
| 2022/0040262 A1 | 2/2022 | Kwon et al. |
| 2022/0054414 A1 | 2/2022 | Mehrnia et al. |
| 2022/0054642 A1 | 2/2022 | Webber et al. |
| 2022/0062190 A1 | 3/2022 | Lucas et al. |
| 2022/0168230 A1 | 6/2022 | Zhou et al. |
| 2022/0175719 A1 | 6/2022 | Cave et al. |
| 2022/0202844 A1 | 6/2022 | Kaufman |
| 2022/0226480 A1 | 7/2022 | Chen et al. |
| 2022/0241238 A1 | 8/2022 | Roth et al. |
| 2022/0249539 A1 | 8/2022 | Linder et al. |
| 2022/0273562 A1 | 9/2022 | Tonge |
| 2022/0280604 A1 | 9/2022 | Orbach et al. |
| 2022/0298225 A1 | 9/2022 | Hubbell et al. |
| 2022/0323905 A1 | 10/2022 | Sung et al. |
| 2022/0364123 A1 | 11/2022 | Gay et al. |
| 2022/0370679 A1 | 11/2022 | Vatankhan-Varnosfaderani et al. |
| 2022/0386594 A1 | 12/2022 | Oren-Benaroya et al. |
| 2022/0401579 A1 | 12/2022 | Williams, III et al. |
| 2022/0402977 A1 | 12/2022 | Hoffmann et al. |
| 2022/0409748 A1 | 12/2022 | Katz |
| 2023/0040206 A1 | 2/2023 | Shah et al. |
| 2023/0115304 A1 | 4/2023 | Baird et al. |
| 2023/0118045 A1 | 4/2023 | Danek |
| 2023/0147292 A1 | 5/2023 | Ezra |
| 2023/0149318 A1 | 5/2023 | Lucas et al. |
| 2023/0183186 A1 | 6/2023 | Hunt et al. |

(56) References Cited

U.S. PATENT DOCUMENTS

| 2023/0210771 | A1 | 7/2023 | Sloat et al. |
|---|---|---|---|
| 2023/0218733 | A1 | 7/2023 | Moomiaie et al. |
| 2023/0233466 | A1 | 7/2023 | Sloat et al. |
| 2023/0234096 | A1 | 7/2023 | Caruso et al. |
| 2023/0235510 | A1 | 7/2023 | Caruso et al. |
| 2023/0240347 | A1 | 8/2023 | Hazen et al. |
| 2023/0241213 | A1 | 8/2023 | Moomiaie et al. |
| 2023/0241250 | A1 | 8/2023 | Edelman et al. |
| 2023/0248653 | A1 | 8/2023 | Noel |
| 2023/0248692 | A1 | 8/2023 | Raskin |
| 2023/0257353 | A1 | 8/2023 | Miao |
| 2023/0270678 | A1 | 8/2023 | Ezra |
| 2023/0270688 | A1 | 8/2023 | Lagaron Cabello et al. |
| 2023/0271167 | A1 | 8/2023 | Strehlau et al. |
| 2023/0288116 | A1 | 9/2023 | Owens, III et al. |
| 2023/0302124 | A1 | 9/2023 | Tan et al. |
| 2023/0321031 | A1 | 10/2023 | Magdassi et al. |
| 2023/0345992 | A1 | 11/2023 | Ezra |
| 2023/0349869 | A1 | 11/2023 | Moorman et al. |
| 2023/0372345 | A1 | 11/2023 | Ogburn et al. |
| 2023/0407276 | A1 | 12/2023 | Doudna et al. |
| 2023/0413823 | A1 | 12/2023 | Ostroff et al. |
| 2023/0417731 | A1 | 12/2023 | Hudson et al. |
| 2024/0000807 | A1 | 1/2024 | Smith |
| 2024/0002358 | A1 | 1/2024 | Meckler et al. |
| 2024/0002846 | A1 | 1/2024 | Liedtke et al. |
| 2024/0009119 | A1 | 1/2024 | Ridall et al. |
| 2024/0050450 | A1 | 2/2024 | Ogburn et al. |
| 2024/0075128 | A1 | 3/2024 | Yantasee et al. |
| 2024/0075182 | A1 | 3/2024 | Cahill et al. |
| 2024/0091145 | A1 | 3/2024 | Bianco-Peled et al. |
| 2024/0091410 | A1 | 3/2024 | Baum et al. |
| 2024/0101642 | A1 | 3/2024 | Lefkowitz et al. |
| 2024/0180987 | A1 | 6/2024 | Elzufon et al. |
| 2024/0182688 | A1 | 6/2024 | Ganesan et al. |
| 2024/0206475 | A1 | 6/2024 | Spadafora et al. |
| 2024/0207146 | A1 | 6/2024 | Wilmott et al. |
| 2024/0207147 | A1 | 6/2024 | Wilmott et al. |
| 2024/0251801 | A1 | 8/2024 | Biggs et al. |
| 2024/0261227 | A1 | 8/2024 | Ogburn et al. |
| 2024/0269318 | A1 | 8/2024 | Schroeder et al. |
| 2024/0307342 | A1 | 9/2024 | Wu et al. |
| 2024/0307474 | A1 | 9/2024 | Al Jasim et al. |
| 2024/0334945 | A1 | 10/2024 | Deng et al. |
| 2024/0351998 | A1 | 10/2024 | Aoyama et al. |
| 2024/0358650 | A1 | 10/2024 | Ogburn et al. |
| 2024/0374519 | A1 | 11/2024 | Sandoval et al. |
| 2024/0391886 | A1 | 11/2024 | Wang et al. |
| 2025/0000806 | A1 | 1/2025 | Ogburn et al. |
| 2025/0018043 | A1 | 1/2025 | Garland et al. |
| 2025/0027950 | A1 | 1/2025 | Hudson et al. |
| 2025/0037565 | A1 | 1/2025 | Hummer et al. |
| 2025/0057891 | A1 | 2/2025 | Repstad et al. |
| 2025/0074959 | A1 | 3/2025 | Jensen et al. |
| 2025/0092351 | A1 | 3/2025 | Moomiaie et al. |
| 2025/0108082 | A1 | 4/2025 | Nelson et al. |
| 2025/0137169 | A1 | 5/2025 | Paliyath et al. |
| 2025/0170097 | A1 | 5/2025 | Blum et al. |
| 2025/0186598 | A1 | 6/2025 | Fu et al. |

FIGURE 1

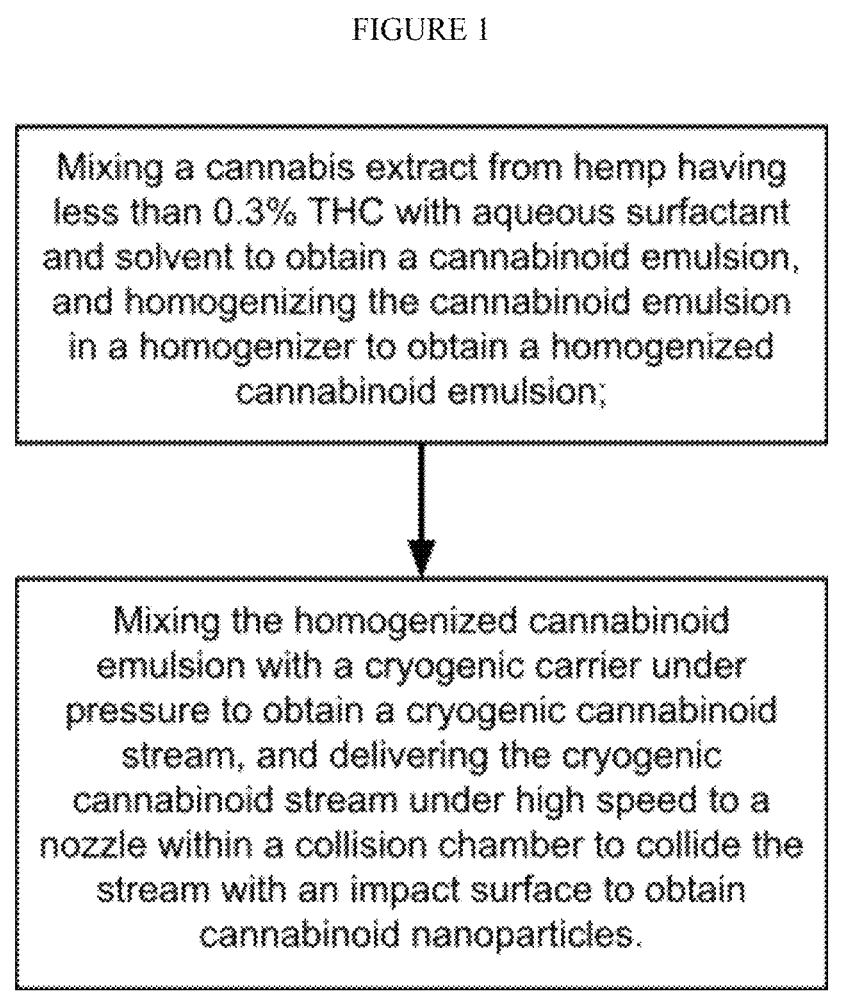

Mixing a cannabis extract from hemp having less than 0.3% THC with aqueous surfactant and solvent to obtain a cannabinoid emulsion, and homogenizing the cannabinoid emulsion in a homogenizer to obtain a homogenized cannabinoid emulsion;

Mixing the homogenized cannabinoid emulsion with a cryogenic carrier under pressure to obtain a cryogenic cannabinoid stream, and delivering the cryogenic cannabinoid stream under high speed to a nozzle within a collision chamber to collide the stream with an impact surface to obtain cannabinoid nanoparticles.

FIGURE 3

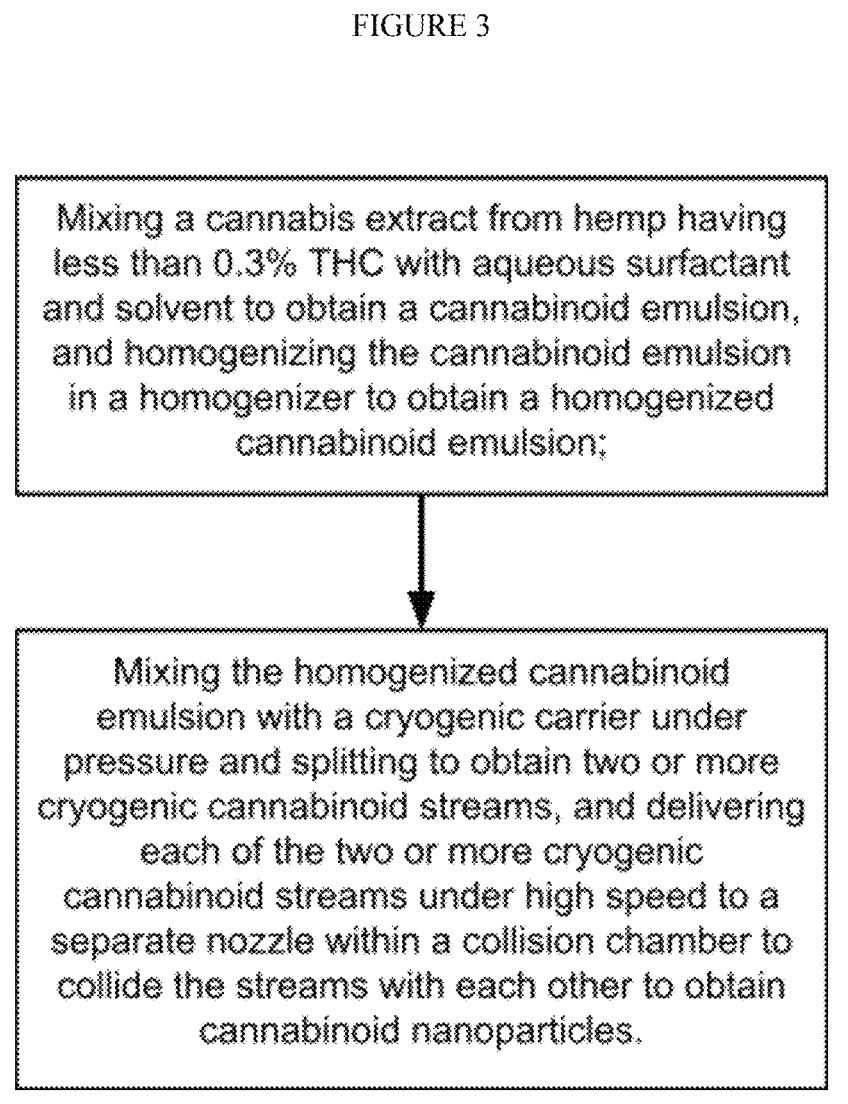

Mixing a cannabis extract from hemp having less than 0.3% THC with aqueous surfactant and solvent to obtain a cannabinoid emulsion, and homogenizing the cannabinoid emulsion in a homogenizer to obtain a homogenized cannabinoid emulsion;

Mixing the homogenized cannabinoid emulsion with a cryogenic carrier under pressure and splitting to obtain two or more cryogenic cannabinoid streams, and delivering each of the two or more cryogenic cannabinoid streams under high speed to a separate nozzle within a collision chamber to collide the streams with each other to obtain cannabinoid nanoparticles.

FIGURE 5

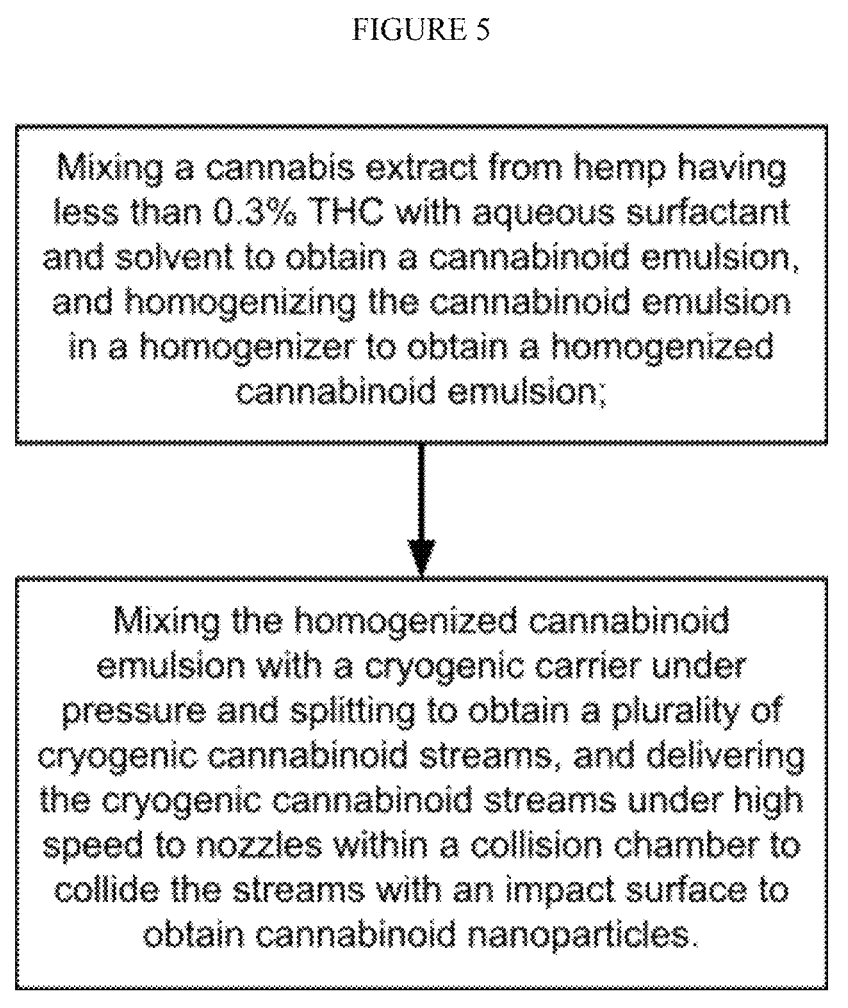

Mixing a cannabis extract from hemp having less than 0.3% THC with aqueous surfactant and solvent to obtain a cannabinoid emulsion, and homogenizing the cannabinoid emulsion in a homogenizer to obtain a homogenized cannabinoid emulsion;

Mixing the homogenized cannabinoid emulsion with a cryogenic carrier under pressure and splitting to obtain a plurality of cryogenic cannabinoid streams, and delivering the cryogenic cannabinoid streams under high speed to nozzles within a collision chamber to collide the streams with an impact surface to obtain cannabinoid nanoparticles.

1. Backing/Roughing Vacuum Pump (Chamber)
2. Diffusion (High Vacuum)
3. Rough Vacuum Pump (Degasser)
4. Trap (Degasser)
5. Trap (Degasser)
6. Liquid Transfer Pump
7. Check Valve
8. Degasser Heater
9. Rotor Heater
10. Vacuum Chamber w/ Condenser
11. Rotor
12. Variable Speed Liquid Transfer Pump
    P - vacuum pressure gauge

FIGURE 8

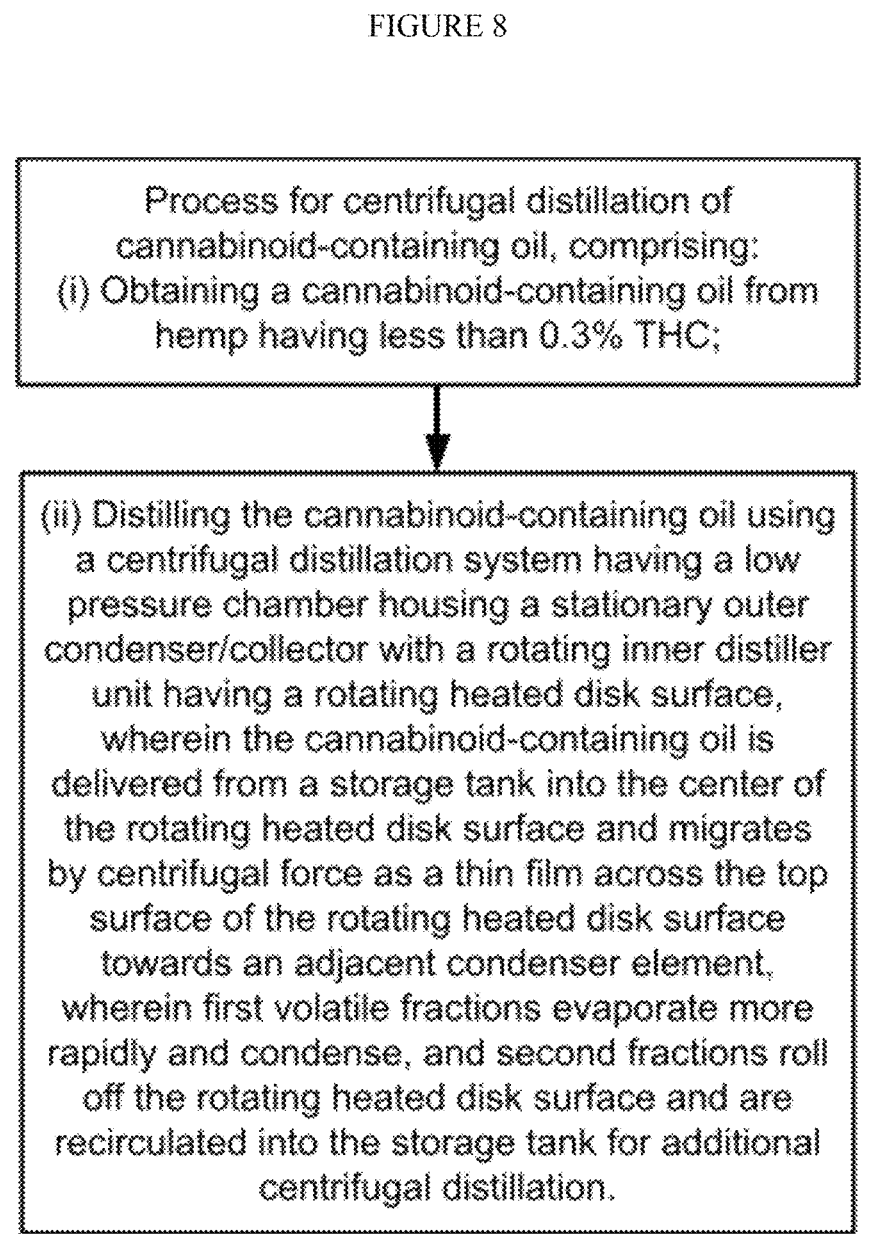

Process for centrifugal distillation of
cannabinoid-containing oil, comprising:
(i) Obtaining a cannabinoid-containing oil from
hemp having less than 0.3% THC;

(ii) Distilling the cannabinoid-containing oil using
a centrifugal distillation system having a low
pressure chamber housing a stationary outer
condenser/collector with a rotating inner distiller
unit having a rotating heated disk surface,
wherein the cannabinoid-containing oil is
delivered from a storage tank into the center of
the rotating heated disk surface and migrates
by centrifugal force as a thin film across the top
surface of the rotating heated disk surface
towards an adjacent condenser element,
wherein first volatile fractions evaporate more
rapidly and condense, and second fractions roll
off the rotating heated disk surface and are
recirculated into the storage tank for additional
centrifugal distillation.

FIGURE 9

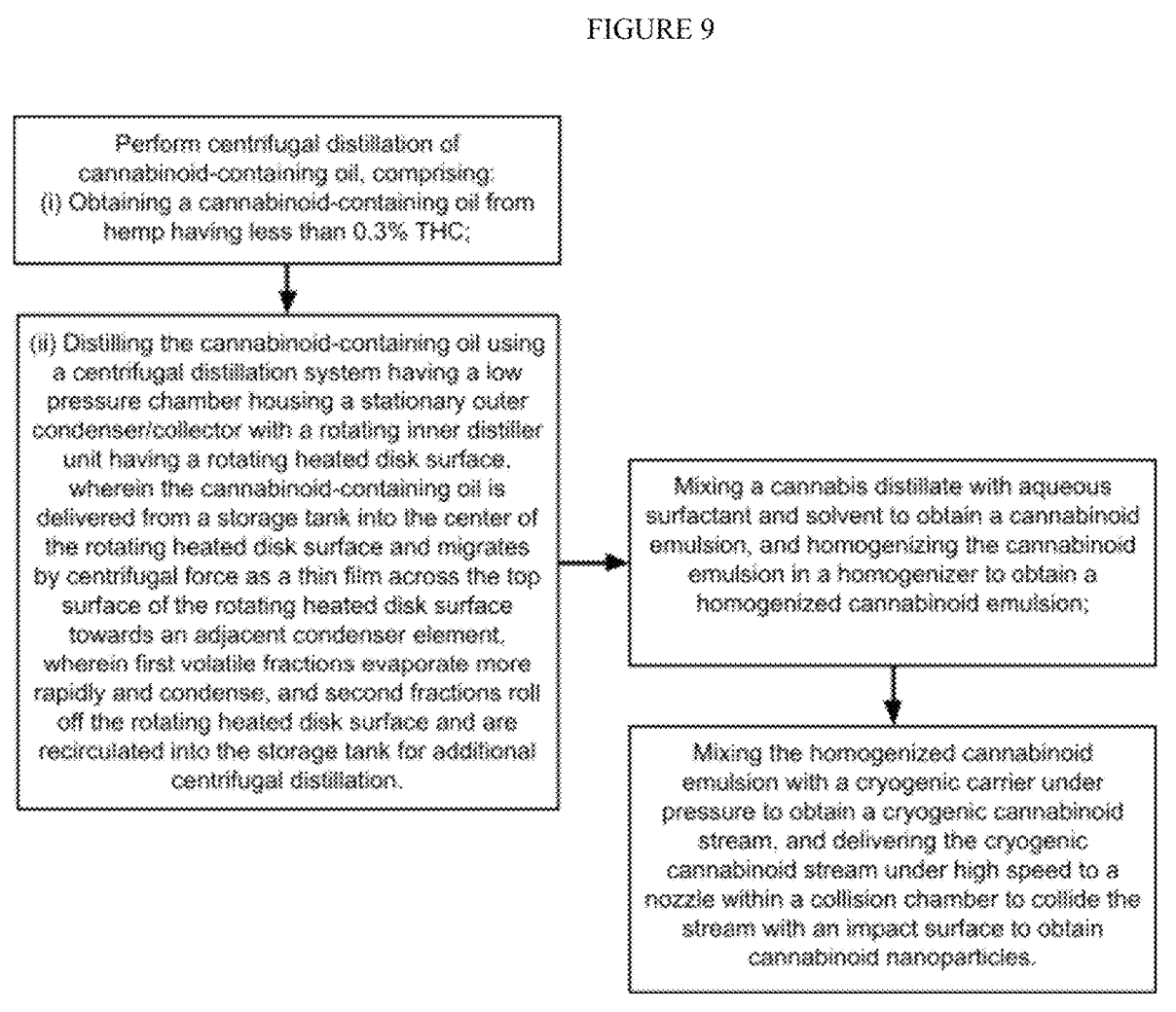

Perform centrifugal distillation of
cannabinoid-containing oil, comprising:
(i) Obtaining a cannabinoid-containing oil from
hemp having less than 0.3% THC;

(ii) Distilling the cannabinoid-containing oil using
a centrifugal distillation system having a low
pressure chamber housing a stationary outer
condenser/collector with a rotating inner distiller
unit having a rotating heated disk surface,
wherein the cannabinoid-containing oil is
delivered from a storage tank into the center of
the rotating heated disk surface and migrates
by centrifugal force as a thin film across the top
surface of the rotating heated disk surface
towards an adjacent condenser element,
wherein first volatile fractions evaporate more
rapidly and condense, and second fractions roll
off the rotating heated disk surface and are
recirculated into the storage tank for additional
centrifugal distillation.

Mixing a cannabis distillate with aqueous
surfactant and solvent to obtain a cannabinoid
emulsion, and homogenizing the cannabinoid
emulsion in a homogenizer to obtain a
homogenized cannabinoid emulsion;

Mixing the homogenized cannabinoid
emulsion with a cryogenic carrier under
pressure to obtain a cryogenic cannabinoid
stream, and delivering the cryogenic
cannabinoid stream under high speed to a
nozzle within a collision chamber to collide the
stream with an impact surface to obtain
cannabinoid nanoparticles.

FIGURE 10

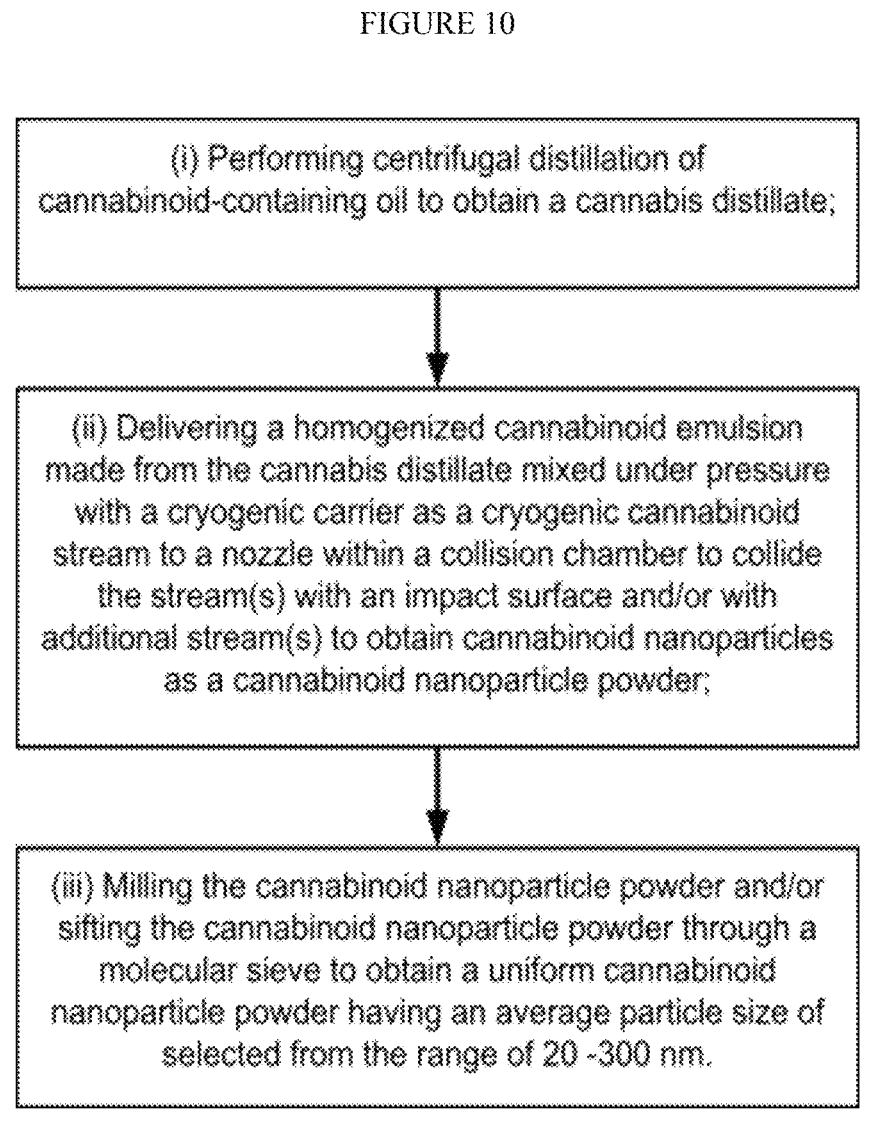

(i) Performing centrifugal distillation of cannabinoid-containing oil to obtain a cannabis distillate;

(ii) Delivering a homogenized cannabinoid emulsion made from the cannabis distillate mixed under pressure with a cryogenic carrier as a cryogenic cannabinoid stream to a nozzle within a collision chamber to collide the stream(s) with an impact surface and/or with additional stream(s) to obtain cannabinoid nanoparticles as a cannabinoid nanoparticle powder;

(iii) Milling the cannabinoid nanoparticle powder and/or sifting the cannabinoid nanoparticle powder through a molecular sieve to obtain a uniform cannabinoid nanoparticle powder having an average particle size of selected from the range of 20 -300 nm.

FIGURE 11

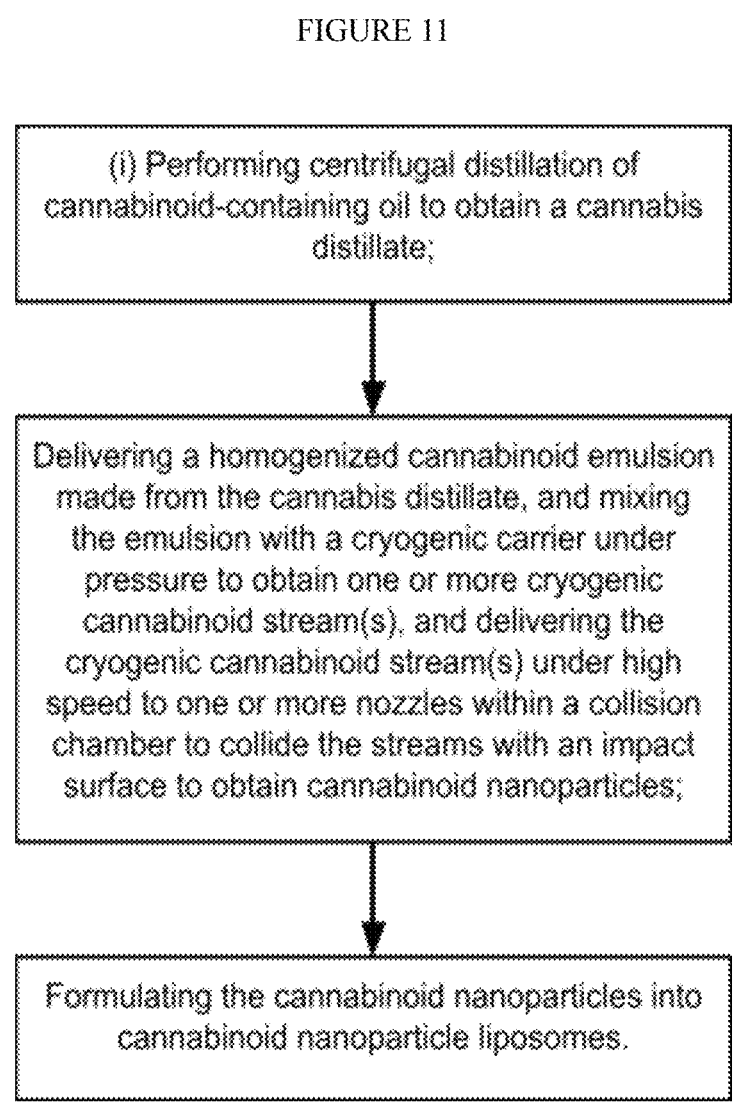

```
┌─────────────────────────────────────────────┐
│      (i) Performing centrifugal distillation of │
│  cannabinoid-containing oil to obtain a cannabis │
│                   distillate;                  │
└─────────────────────────────────────────────┘
                        │
                        ▼
┌─────────────────────────────────────────────┐
│   Delivering a homogenized cannabinoid emulsion │
│      made from the cannabis distillate, and mixing │
│      the emulsion with a cryogenic carrier under │
│        pressure to obtain one or more cryogenic │
│       cannabinoid stream(s), and delivering the │
│       cryogenic cannabinoid stream(s) under high │
│    speed to one or more nozzles within a collision │
│      chamber to collide the streams with an impact │
│     surface to obtain cannabinoid nanoparticles; │
└─────────────────────────────────────────────┘
                        │
                        ▼
┌─────────────────────────────────────────────┐
│   Formulating the cannabinoid nanoparticles into │
│       cannabinoid nanoparticle liposomes.       │
└─────────────────────────────────────────────┘
```

FIGURE 12

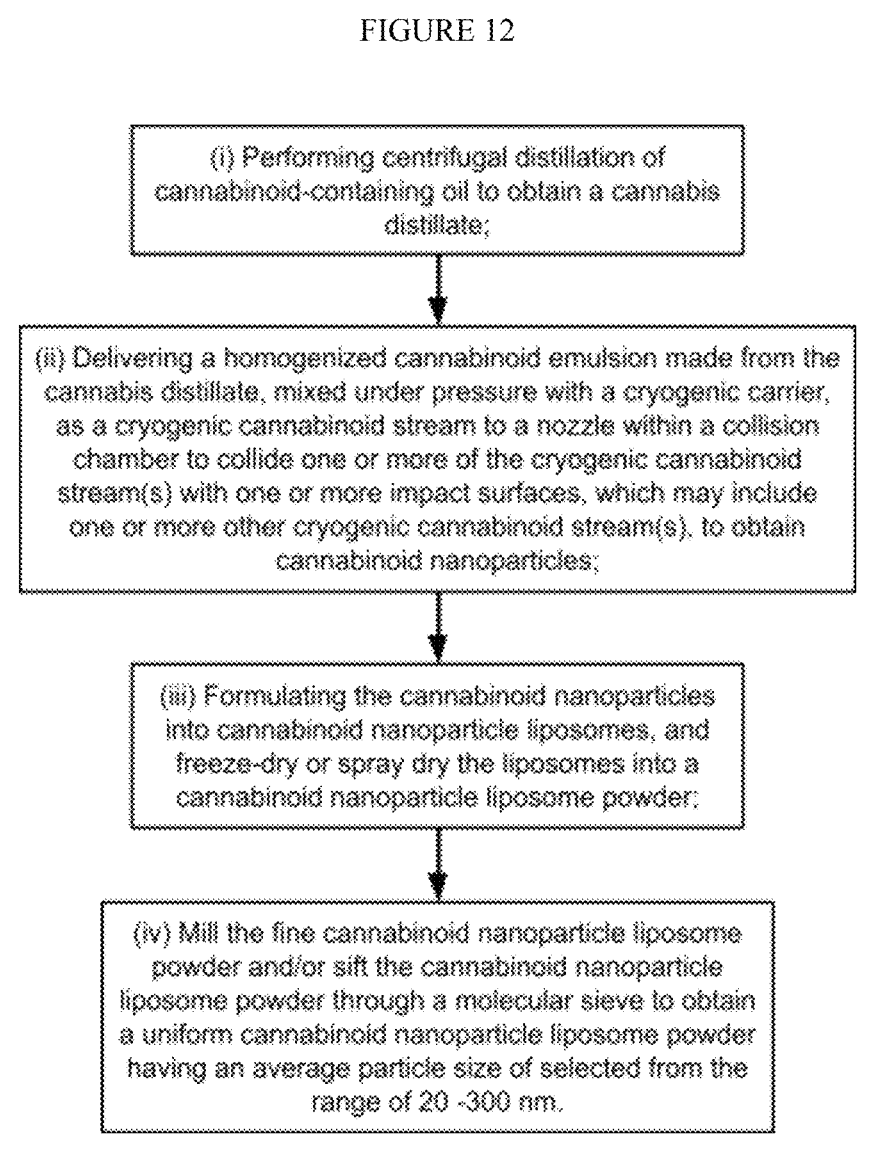

(i) Performing centrifugal distillation of cannabinoid-containing oil to obtain a cannabis distillate;

(ii) Delivering a homogenized cannabinoid emulsion made from the cannabis distillate, mixed under pressure with a cryogenic carrier, as a cryogenic cannabinoid stream to a nozzle within a collision chamber to collide one or more of the cryogenic cannabinoid stream(s) with one or more impact surfaces, which may include one or more other cryogenic cannabinoid stream(s), to obtain cannabinoid nanoparticles;

(iii) Formulating the cannabinoid nanoparticles into cannabinoid nanoparticle liposomes, and freeze-dry or spray dry the liposomes into a cannabinoid nanoparticle liposome powder;

(iv) Mill the fine cannabinoid nanoparticle liposome powder and/or sift the cannabinoid nanoparticle liposome powder through a molecular sieve to obtain a uniform cannabinoid nanoparticle liposome powder having an average particle size of selected from the range of 20 -300 nm.

FIGURE 13

Cryogenic fluids with their boiling point in Kelvin and degree Celsius.

| Fluid | Boiling point (K) | Boiling point (°C) |
|---|---|---|
| Helium-3 | 3.19 | -269.96 |
| Helium-4 | 4.214 | -268.936 |
| Hydrogen | 20.27 | -252.88 |
| Neon | 27.09 | -246.06 |
| Nitrogen | 77.09 | -196.06 |
| Air | 78.8 | -194.35 |
| Fluorine | 85.24 | -187.91 |
| Argon | 87.24 | -185.91 |
| Oxygen | 90.18 | -182.97 |
| Methane | 111.7 | -161.45 |

FIGURE 14

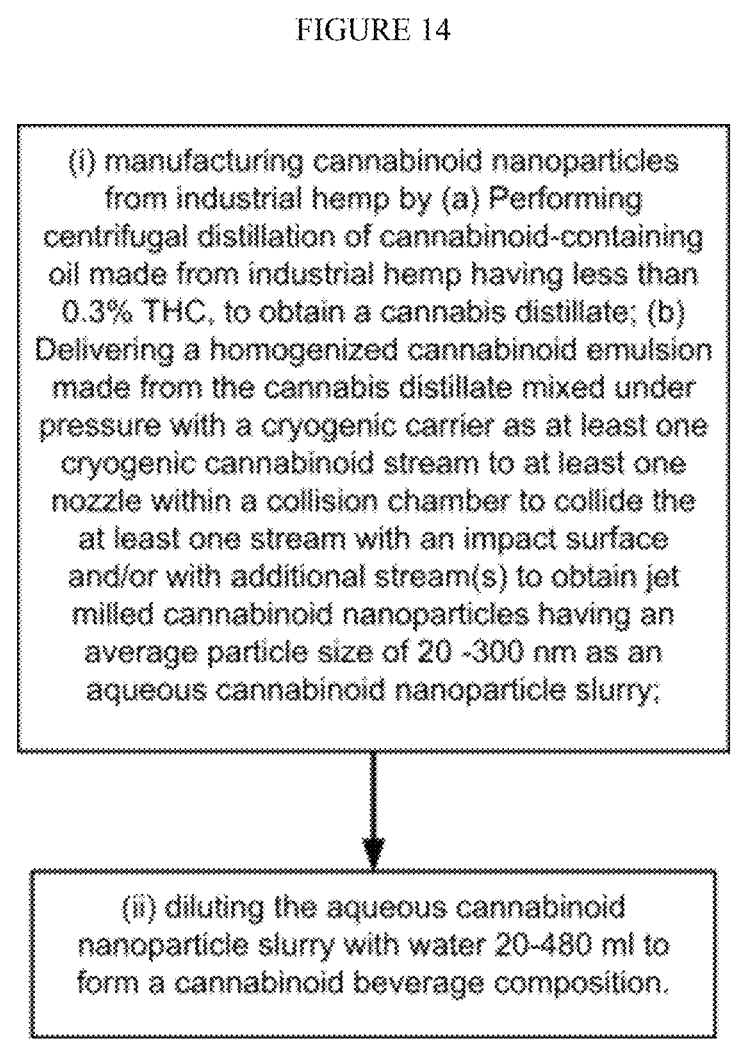

(i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20 -300 nm as an aqueous cannabinoid nanoparticle slurry;

(ii) diluting the aqueous cannabinoid nanoparticle slurry with water 20-480 ml to form a cannabinoid beverage composition.

FIGURE 15

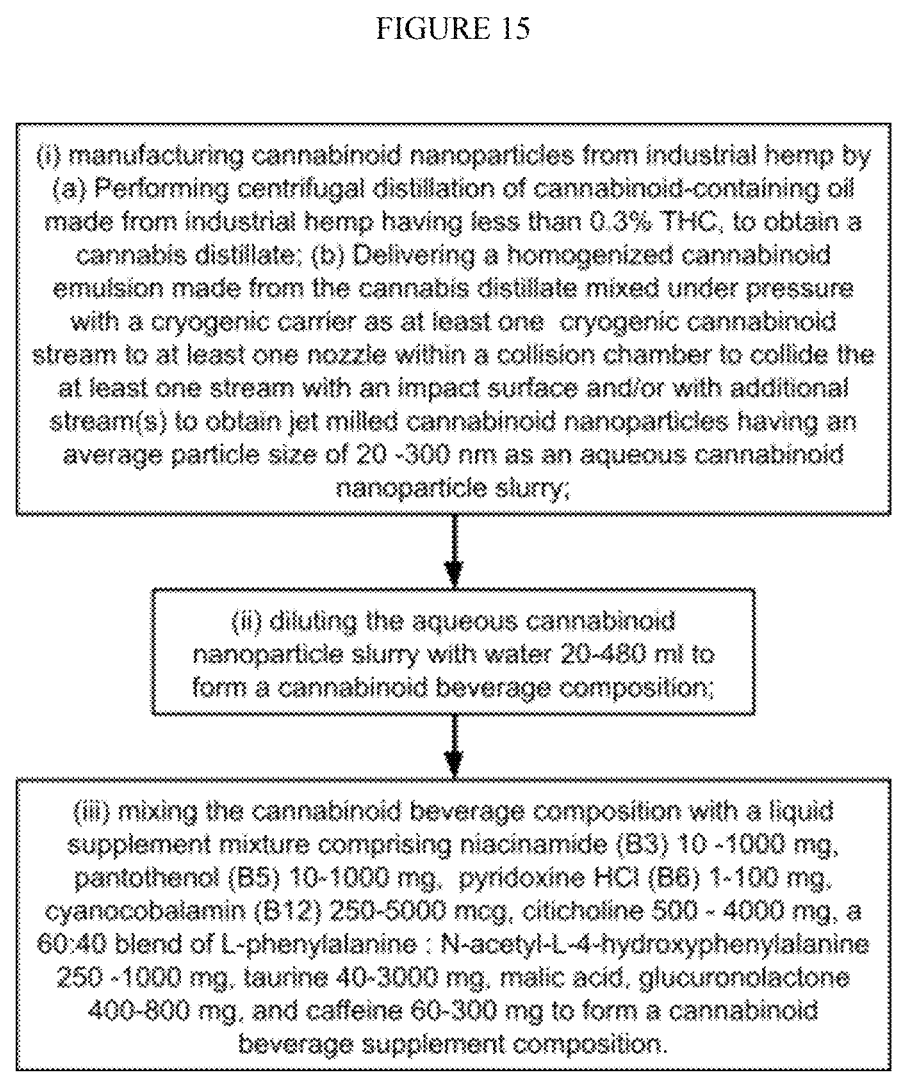

(i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20 -300 nm as an aqueous cannabinoid nanoparticle slurry;

(ii) diluting the aqueous cannabinoid nanoparticle slurry with water 20-480 ml to form a cannabinoid beverage composition;

(iii) mixing the cannabinoid beverage composition with a liquid supplement mixture comprising niacinamide (B3) 10 -1000 mg, pantothenol (B5) 10-1000 mg, pyridoxine HCl (B6) 1-100 mg, cyanocobalamin (B12) 250-5000 mcg, citicholine 500 - 4000 mg, a 60:40 blend of L-phenylalanine : N-acetyl-L-4-hydroxyphenylalanine 250 -1000 mg, taurine 40-3000 mg, malic acid, glucuronolactone 400-800 mg, and caffeine 60-300 mg to form a cannabinoid beverage supplement composition.

FIGURE 16

(i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20 -300 nm as an aqueous cannabinoid nanoparticle slurry;

(ii) diluting the aqueous cannabinoid nanoparticle slurry with water 20-480 ml to form a cannabinoid beverage composition;

(iii) mixing the cannabinoid beverage composition with a liquid supplement mixture comprising niacinamide (B3) 10 -1000 mg, pantothenol (B5) 10-1000 mg, pyridoxine HCl (B6) 1-100 mg, cyanocobalamin (B12) 250-5000 mcg, citicholine 500 - 4000 mg, a 60:40 blend of L-phenylalanine : N-acetyl-L-4-hydroxyphenylalanine 250 -1000 mg, taurine 40-3000 mg, malic acid, glucuronolactone 400-800 mg, and caffeine 60-300 mg to form a cannabinoid beverage supplement composition;

(iv) mixing the cannabinoid beverage composition with a secondary liquid supplement comprising Vitamin C, Vitamin D, Vitamin E, zinc, magnesium, manganese, copper, potassium, and selenium to form an enhanced cannabinoid beverage supplement composition.

FIGURE 17

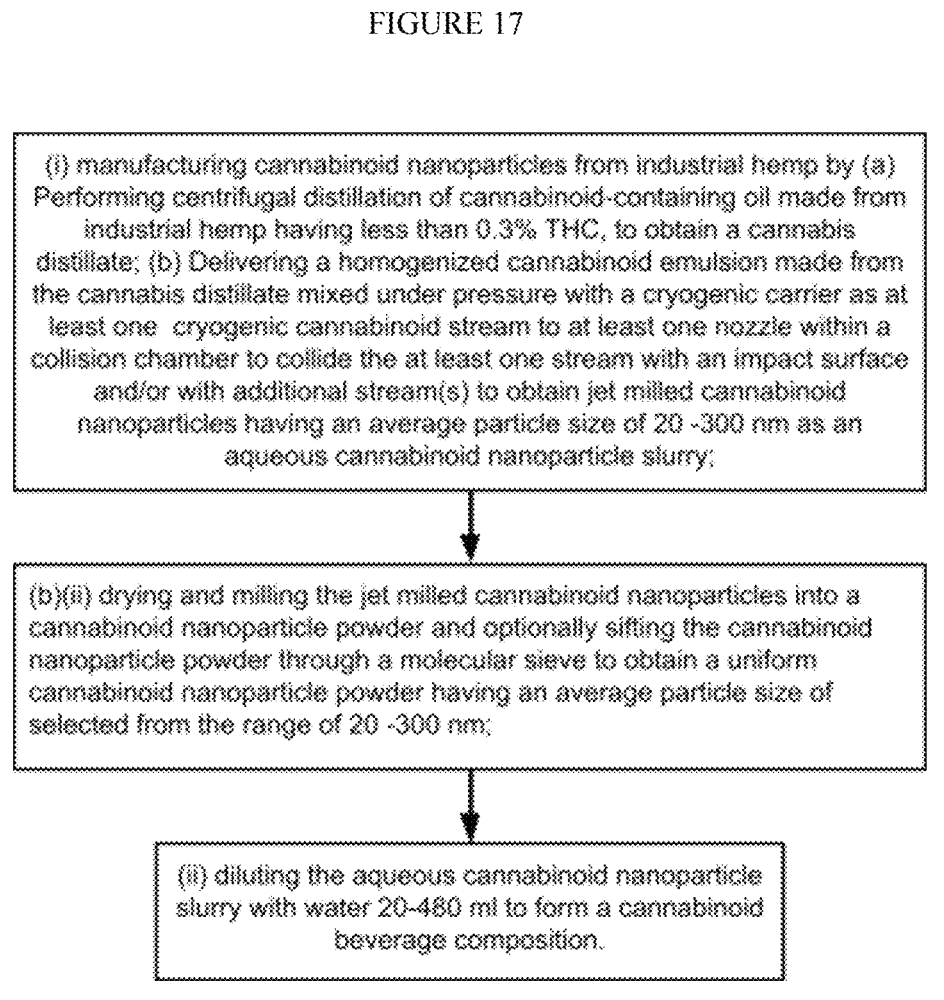

(i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20 -300 nm as an aqueous cannabinoid nanoparticle slurry;

(b)(ii) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20 -300 nm;

(ii) diluting the aqueous cannabinoid nanoparticle slurry with water 20-480 ml to form a cannabinoid beverage composition.

FIGURE 18

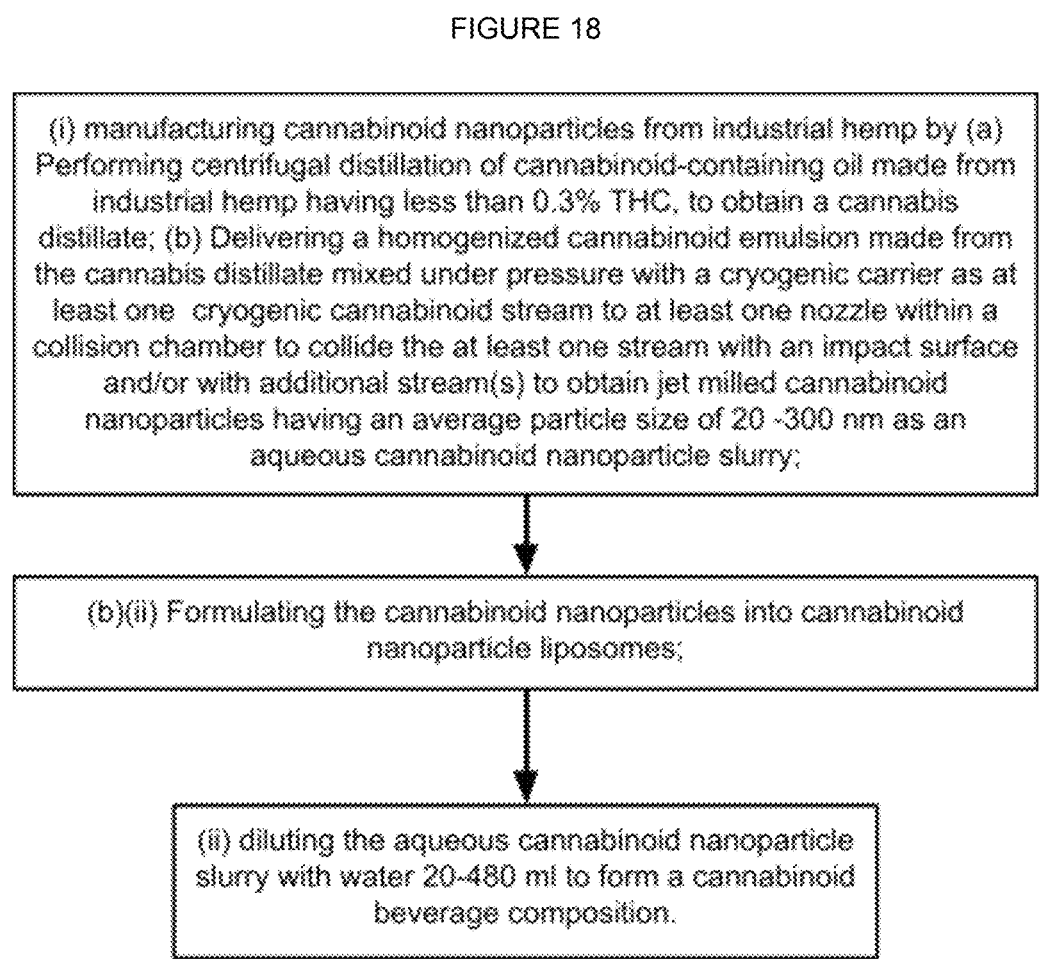

(i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20 -300 nm as an aqueous cannabinoid nanoparticle slurry;

⬇

(b)(ii) Formulating the cannabinoid nanoparticles into cannabinoid nanoparticle liposomes;

⬇

(ii) diluting the aqueous cannabinoid nanoparticle slurry with water 20-480 ml to form a cannabinoid beverage composition.

COMPOSITIONS CONTAINING CANNABINOID NANOPARTICLES

FIELD OF THE INVENTION

The invention relates generally to beverage compositions comprising cryogenically produced cannabinoid nanoparticles using cannabinoids made from hemp, and processes for making the same.

BACKGROUND

Producing nanoparticles made from chemical and biological compounds can pose engineering challenges depending on the compounds chosen and the characteristics of the particles being sought. Producing nanoparticles directly from the compounds themselves is a different challenge than adhering or encapsulating an active compound within a nano-scale carrier particle such as liposomes, micelles, shells, or even conjugating to nano-scale carrier compounds, nano-scale metal powders, nano-scale polymers, or nano-scale biologics such as proteins, amino acids, various organic sugars, or organic salts.

Some of the engineering challenges relate to the nanoparticle compounds include solubility, charge, purity, temperature, crystallization, stereochemistry, and stability. Other engineering challenges relate to the nanoparticle aspect and include the process for making the nanoparticles, characterizing the nanoparticles, analyzing nanoparticle size and size distribution, analyzing nanoparticle density, solubility, surface charge, surface chemistry and morphology, surface adhesion, purity, temperature, and stability.

Technologies for making nanoparticles can include grinding, milling, atomization, spray drying, homogenization, sonication, use of solvents, centrifugation, filtering, and lyophilization. As the desired size of the particles shrinks from micrometer to nanometer scale, the selection of process parameters and techniques become more critical and the processes more difficult.

Cannabis has more than 400 bioactive components, the majority of which are cannabinoids or phytocannabinoids, polyphenols, flavonoids, terpenes, terpenoids, fatty acids, oils and waxes. Cannabinoids which are useful for commercial and therapeutic uses are tetrahydrocannabinol, cannabidiol, cannabinol as well as their carboxylic acid derivatives and cannabis-derived terpenes.

However, cannabinoids are known for the processing and handling difficulty they present, especially when attempting to produce cannabinoids that can be used in commercial or therapeutic applications. Additionally, much of the cannabis industry generates cannabinoid products that do not have pure ingredients, have toxic impurities, do not contain what the label says they contain, and are not safely produced using Current Good Manufacturing Practice (CGMP) regulations enforced by the FDA, and as such suffer from the lack of oversight, purity, and reproducibility.

Accordingly, a need exists for beverage compositions comprising cryogenically produced cannabinoid nanoparticles using cannabinoids made from hemp, and processes for making the same to solve these and other problems in the art.

SUMMARY

The embodiments described herein are directed to a cannabinoid beverage composition, comprising: (i) water; and (ii) cannabinoid nanoparticles 1-30 mg with at least one dimension less than 100 nm.

In one non-limiting preferred embodiment, the invention provides a cannabinoid beverage composition, comprising: (i) water 20-480 ml; (ii) cannabinoid nanoparticles 1-30 mg with at least one dimension less than 100 nm.

In another non-limiting preferred embodiment, the invention provides a cannabinoid beverage composition, comprising: (i) water; and (ii) cannabinoid nanoparticles 1-30 mg with at least one dimension less than 100 nm; (iii) a mixture of niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, caffeine 60-300 mg; and optionally (iv) Vitamin C, Vitamin D, Vitamin E, zinc, magnesium, manganese, copper, potassium, selenium.

In another non-limiting preferred embodiment, the invention provides a cannabinoid beverage composition, comprising: (i) water 44-60 ml; (ii) cannabinoid nanoparticles 1-30 mg with at least one dimension less than 100 nm; (iii) a mixture of niacinamide (B3) 40 mg, pyridoxine HCl (B6) 40 mg, cyanocobalamin (B12) 500 mcg, citicholine 10-1000 mg, a 60:40 blend of L-phenylalanine:N-acetyl-L-4-hydroxyphenylalanine 250-1000 mg, taurine 10-3000 mg, malic acid, glucuronolactone 100-1000 mg, caffeine 60-250 mg.

In another non-limiting preferred embodiment, the invention provides a cannabinoid beverage composition, comprising: (i) water; and (ii) cannabinoid nanoparticles 1-30 mg with at least one dimension less than 100 nm, wherein the cannabinoid nanoparticles are an aqueous slurry.

In another non-limiting preferred embodiment, the invention provides a cannabinoid beverage composition, comprising: (i) water; and (ii) cannabinoid nanoparticles 1-30 mg with at least one dimension less than 100 nm, wherein the cannabinoid nanoparticles are a powder having a surfactant coating In another non-limiting preferred embodiment, the invention provides a cannabinoid beverage composition, comprising: (i) water; and (ii) cannabinoid nanoparticles 1-30 mg wherein the cannabinoid nanoparticles are with at least one dimension less than 50 nm.

In another non-limiting preferred embodiment, the invention provides a process for making a cannabinoid beverage composition, comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Preparing a homogenized cannabinoid emulsion from the cannabis distillate mixed with aqueous surfactant and solvent, and delivering the homogenized cannabinoid emulsion under pressure with a cryogenic carrier fluid as a cryogenic cannabinoid stream to at least one nozzle within a collision chamber to collide the cryogenic cannabinoid stream with an impact surface and/or with one or more additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition.

In another non-limiting preferred embodiment, the process includes (iii) mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition; and (v) optionally mixing the cannabinoid beverage composition with a secondary liquid supplement comprising Vitamin C, Vitamin D, Vitamin E, zinc, magnesium, manganese, copper, potassium, and selenium to form an enhanced cannabinoid beverage supplement composition.

In another preferred embodiment, the invention provides wherein the process for manufacturing a cannabinoid beverage composition containing cannabinoid nanoparticles from industrial hemp further comprises the step of: (b)(ii) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm.

In another preferred embodiment, the invention provides wherein the process for manufacturing a cannabinoid beverage composition containing cannabinoid nanoparticles from industrial hemp further comprises the step: (b)(ii) Formulating the cannabinoid nanoparticles into cannabinoid nanoparticle liposomes.

In another preferred embodiment, the invention provides wherein the process for manufacturing a cannabinoid beverage composition containing cannabinoid nanoparticles from industrial hemp further comprises the step: drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm.

In a preferred embodiment, the invention provides a composition comprising cannabinoid nanoparticles having an average size less than 200 nm, and even a composition comprising cannabinoid nanoparticles having an average size less than 100 nm.

In a preferred embodiment, the invention comprises cannabinoid nanoparticles formulated as a nanosuspension, or as a nanoemulsion.

BRIEF DESCRIPTION OF THE DRAWINGS

FIG. 1 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles.

FIG. 3 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and splitting to obtain two or more cryogenic cannabinoid streams, and delivering each of the two or more cryogenic cannabinoid streams under high speed to a separate nozzle within a collision chamber to collide the streams with each other to obtain cannabinoid nanoparticles.

FIG. 5 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles.

FIG. 8 is a flowchart illustrating a non-limiting preferred embodiment of the process using the centrifugal distillation system.

FIG. 9 is a flowchart illustrating a non-limiting preferred embodiment of a combined process to make cannabinoid nanoparticle from centrifugally distilled cannabinoid-containing oil, comprising the steps of: (i) performing centrifugal distillation of a cannabinoid-containing oil, preferably a cannabinoid-containing oil from hemp having less than 0.3% THC; (ii) mixing the cannabis distillate with aqueous surfactant and solvent to obtain a cannabinoid emulsion, and homogenizing the cannabinoid emulsion in a homogenizer to obtain a homogenized cannabinoid emulsion; and (iii) mixing the homogenized cannabinoid emulsion with a cryogenic carrier under pressure to obtain a cryogenic cannabinoid stream, and delivering the cryogenic cannabinoid stream under high speed to a nozzle within a collision chamber to collide the stream with an impact surface to obtain cannabinoid nanoparticles.

FIG. 10 is a flowchart illustrating a non-limiting preferred embodiment of a combined process to make cannabinoid nanoparticle powder comprising the steps: (i) Perform centrifugal distillation of cannabinoid-containing oil to obtain a cannabis distillate; (ii) Deliver a homogenized cannabinoid emulsion made from the cannabis distillate mixed under pressure with a cryogenic carrier as a cryogenic cannabinoid stream to a nozzle within a collision chamber to collide the stream(s) with an impact surface and/or with additional stream(s) to obtain cannabinoid nanoparticles as a cannabinoid nanoparticle powder; (iii) Mill the cannabinoid nanoparticle powder and/or sift the cannabinoid nanoparticle powder through a molecular sieve to obtain a uniform cannabinoid nanoparticle powder having an average particle size of selected from the range of 20-300 nm.

FIG. 11 is a flowchart illustrating a non-limiting preferred embodiment of a combined process to make cannabinoid nanoparticle liposomes comprising the steps of: (i) performing centrifugal distillation of a cannabinoid-containing oil to obtain a cannabis distillate; and then (ii) preparing a homogenized cannabinoid emulsion from the cannabis distillate to mix the emulsion with a cryogenic carrier under pressure to obtain a cryogenic cannabinoid stream, and deliver the cryogenic cannabinoid stream under high speed to a nozzle within a collision chamber to collide the stream with an impact surface to obtain cannabinoid nanoparticles; and finally (iii) formulating the cannabinoid nanoparticles into cannabinoid nanoparticle liposomes.

FIG. 12 is a flowchart illustrating a non-limiting preferred embodiment of a combined process to make cannabinoid nanoparticle liposome powder comprising the steps of: (i) Perform centrifugal distillation of cannabinoid-containing oil to obtain a cannabis distillate; (ii) Deliver a homogenized cannabinoid emulsion made from the cannabis distillate, with a cryogenic carrier, under pressure as a cryogenic cannabinoid stream to a nozzle within a collision chamber to collide the stream(s) with an impact surface an/or other stream(s) to obtain cannabinoid nanoparticles; (iii) Formulate the cannabinoid nanoparticles into cannabinoid nanoparticle liposomes, and freeze-dry or spray dry the liposomes into a cannabinoid nanoparticle liposome powder; (iv) Mill the fine cannabinoid nanoparticle powder and/or sift the fine cannabinoid nanoparticle powder through a molecular sieve to obtain a uniform cannabinoid nanoparticle powder having an average particle size of selected from the range of 20-300 nm.

FIG. 13 is a chart showing a non-limiting list of cryogenic fluids with their boiling point in Kelvin and degree Celsius.

FIG. 14 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition.

FIG. 15 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition; (iii) mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition.

FIG. 16 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition; (iii) mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition; (iv) mixing the cannabinoid beverage composition with a secondary liquid supplement comprising Vitamin C, Vitamin D, Vitamin E, zinc, magnesium, manganese, copper, potassium, and selenium to form an enhanced cannabinoid beverage supplement composition.

FIG. 17 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (b)(ii) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm; (ii) diluting the aqueous cannabinoid nanoparticle slurry with water 20-480 ml to form a cannabinoid beverage composition.

FIG. 18 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (b)(ii) Formulating the cannabinoid nanoparticles into cannabinoid nanoparticle liposomes; (ii) diluting the aqueous cannabinoid nanoparticle slurry with water 20-480 ml to form a cannabinoid beverage composition.

DETAILED DESCRIPTION OF THE INVENTION

Figure 2:
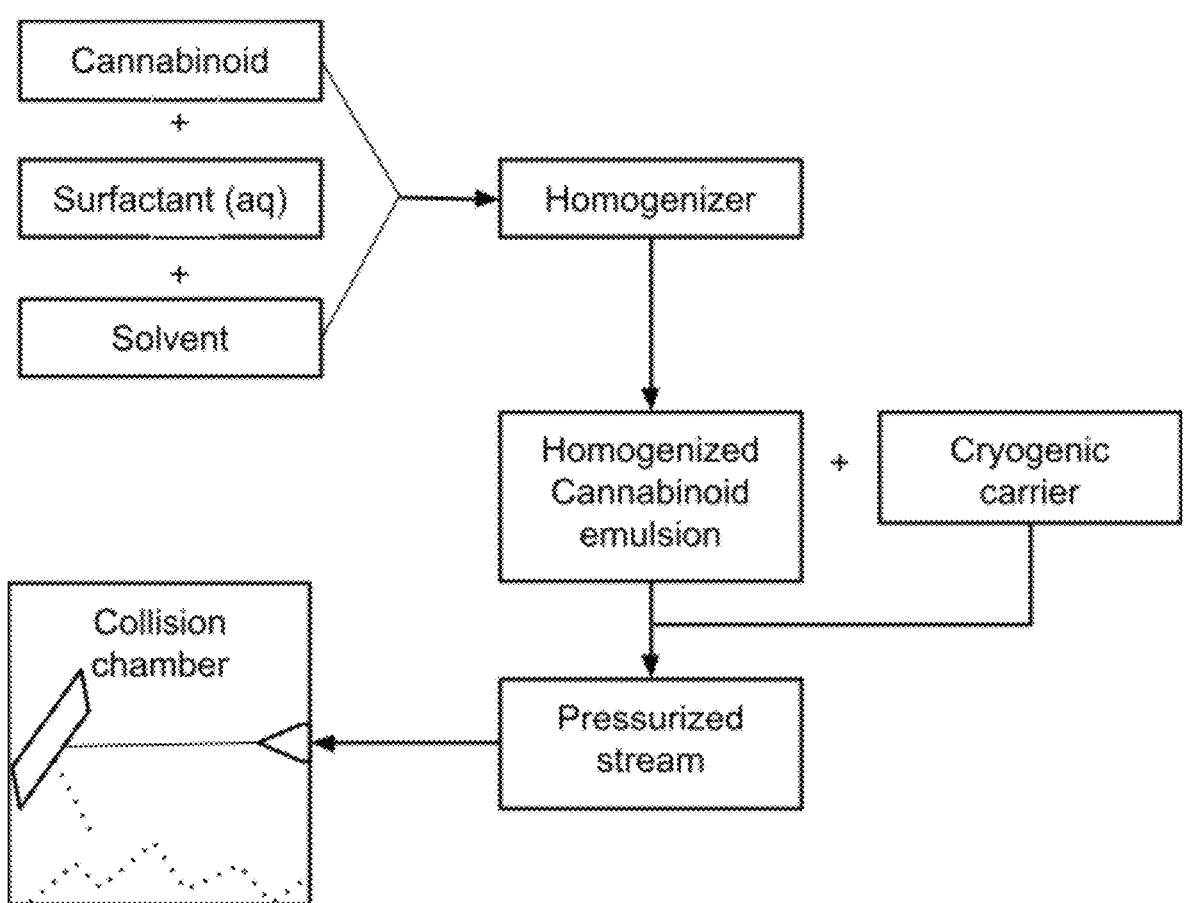
FIG. 2 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles.

Disclosed is a non-limiting preferred embodiment of a cannabinoid beverage composition, comprising: (i) water; and (ii) cannabinoid nanoparticles 1-30 mg with at least one dimension less than 100 nm.

Any of the preferred embodiments herein may include wherein the cannabinoid beverage composition further comprises: (iii) a mixture of niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg, Any of the preferred embodiments herein may include wherein the cannabinoid beverage composition further comprises: Vitamin C, Vitamin D, Vitamin E, zinc, magnesium, manganese, copper, potassium, selenium.

Another non-limiting preferred embodiment provides a cannabinoid beverage composition, comprising: (i) water 44-60 ml; (ii) cannabinoid nanoparticles 1-30 mg with at least one dimension less than 100 nm; (iii) a mixture of niacinamide (B3) 40 mg, pyridoxine HCl (B6) 40 mg, cyanocobalamin (B12) 500 mcg, citicholine 10-1000 mg, a 60:40 blend of L-phenylalanine:N-acetyl-L-4-hydroxyphenylalanine 250-1000 mg, taurine 10-3000 mg, malic acid, glucuronolactone 100-1000 mg, caffeine 60-250 mg.

Any of the preferred embodiments herein may include wherein the cannabinoid nanoparticles are an aqueous slurry.

Any of the preferred embodiments herein may include wherein the cannabinoid nanoparticles are a powder having a surfactant coating.

Any of the preferred embodiments herein may include where the cannabinoid nanoparticles with at least one dimension less than 50 nm.

Any of the preferred embodiments herein may include wherein the water is 20-480 ml.

Any of the preferred embodiments herein may include wherein the water is 44-60 ml.

Any of the preferred embodiments herein may include wherein the cannabinoid nanoparticles are a nanosuspension of a cannabinoid nanoparticle powder having a surfactant coating.

Any of the preferred embodiments herein may include wherein the cannabinoid nanoparticles are with at least one dimension less than 50 nm.

In another non-limiting preferred embodiment, the invention provides a process for manufacturing a cannabinoid beverage composition from cannabinoid nanoparticles made from industrial hemp, comprising the steps: (i) Performing centrifugal distillation of cannabinoid-containing oil made from industrial hemp having less than 0.3% THC, to obtain a cannabis distillate; (ii) Preparing a homogenized cannabinoid emulsion from the cannabis distillate mixed with aqueous surfactant and solvent, and delivering the homogenized cannabinoid emulsion under pressure with a cryogenic carrier fluid as a cryogenic cannabinoid stream to at least one nozzle within a collision chamber to collide the cryogenic cannabinoid stream with an impact surface and/or with one or more additional stream(s) to obtain jet milled cannabinoid nanoparticles having an average particle size of 20-300 nm as an aqueous cannabinoid nanoparticle slurry; (iii) Diluting the aqueous cannabinoid nanoparticle slurry with water 20-480 ml to form a cannabinoid beverage composition; (iv) optionally mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition; and (v) optionally mixing the cannabinoid beverage composition with a secondary liquid supplement comprising Vitamin C, Vitamin D, Vitamin E, zinc, magnesium, manganese, copper, potassium, and selenium to form an enhanced cannabinoid beverage supplement composition.

Any of the preferred processes may further comprise the step of: (ii)(b) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm.

Any of the preferred processes may further comprise the step of: (ii)(b) Formulating the cannabinoid nanoparticles into cannabinoid nanoparticle liposomes.

Any of the preferred processes may further comprise the step of: drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size less than 100 nm.

Any of the preferred processes may further comprise wherein the cannabinoid nanoparticles are formulated as a nanosuspension or as a nanoemulsion.

Also necessarily disclosed are embodiments directed to a cryogenic process for making cannabinoid nanoparticles and compositions made thereby.

As disclosed, in one preferred embodiment the invention provides a process for making cannabinoid nanoparticles, comprising: Obtaining a cannabis concentrate from hemp having less than 0.3% THC; Mixing the cannabis concentrate with aqueous surfactant and solvent to obtain a cannabinoid emulsion; Homogenizing the cannabinoid emulsion in a homogenizer to obtain a homogenized cannabinoid emulsion; Mixing the homogenized cannabinoid emulsion with a cryogenic carrier under pressure to obtain a cryogenic cannabinoid stream; Delivering the cryogenic cannabinoid stream under high speed to a nozzle within a collision chamber to collide the cryogenic cannabinoid stream with an impact surface to obtain cannabinoid nanoparticles; and Collecting cannabinoid nanoparticles from the collision chamber into a reservoir.

In another preferred embodiment, the invention provides a process for manufacturing cannabinoid nanoparticles, comprising the steps: (i) Performing centrifugal distillation of cannabinoid-containing oil, preferably a cannabinoid-containing oil from hemp having less than 0.3% THC, to obtain a cannabis distillate; (ii) Delivering a homogenized cannabinoid emulsion made from the cannabis distillate mixed under pressure with a cryogenic carrier as a cryogenic cannabinoid stream to a nozzle within a collision chamber to collide the stream(s) with an impact surface and/or with additional stream(s) to obtain cannabinoid nanoparticles as a cannabinoid nanoparticle powder.

In another preferred embodiment, the invention provides wherein the process for manufacturing cannabinoid nanoparticles further comprises the step of: (iii) Milling the cannabinoid nanoparticle powder and/or sifting the cannabinoid nanoparticle powder through a molecular sieve to obtain a uniform cannabinoid nanoparticle powder having an average particle size of selected from the range of 20-300 nm.

In another preferred embodiment, the invention provides a cannabinoid nanoparticle composition made by the processes described and claimed herein.

In another preferred embodiment, the invention provides a process for manufacturing cannabinoid nanoparticle liposomes, comprising the steps: (i) Performing centrifugal distillation of cannabinoid-containing oil to obtain a cannabis distillate; (ii) Delivering a homogenized cannabinoid emulsion made from the cannabis distillate, and mixing the emulsion with a cryogenic carrier under pressure to obtain one or more cryogenic cannabinoid stream(s), and delivering the cryogenic cannabinoid stream(s) under high speed to one or more nozzles within a collision chamber to collide the streams with an impact surface to obtain cannabinoid nanoparticles; (iii) Formulating the cannabinoid nanoparticles into cannabinoid nanoparticle liposomes.

In another preferred embodiment, the invention provides wherein the process for manufacturing cannabinoid nanoparticle liposomes, further comprises the step of: (iv) Milling the cannabinoid nanoparticle powder and/or sifting the cannabinoid nanoparticle powder through a molecular sieve to obtain a uniform cannabinoid nanoparticle powder having an average particle size of selected from the range of 20-300 nm.

In another preferred embodiment, the invention provides a cannabinoid nanoparticle liposome composition made by the processes described and claimed herein.

In a preferred embodiment, the invention provides a composition comprising cannabinoid nanoparticles having an average size less than 500 nm, cannabinoid nanoparticles having an average size less than 200 nm, and even cannabinoid nanoparticles have an average size less than 100 nm.

Any of the preferred embodiments herein may include a process wherein the step of collecting cannabinoid nanoparticles from the collision chamber includes passing the collected cannabinoid nanoparticles through a nanofilter or molecular sieve having a pore size less than 500 nm before depositing in the reservoir, and returning collected cannabinoid nanoparticles larger than 500 nm in a return stream to the cryogenic cannabinoid stream.

Any of the preferred embodiments herein may include a process wherein the step of collecting cannabinoid nanoparticles from the collision chamber includes passing the collected cannabinoid nanoparticles through a nanofilter or molecular sieve having a pore size less than 200 nm before depositing in the reservoir, and returning collected cannabinoid nanoparticles larger than 200 nm in a return stream to the cryogenic cannabinoid stream.

Any of the preferred embodiments herein may include a process wherein the step of collecting cannabinoid nanoparticles from the collision chamber includes passing the collected cannabinoid nanoparticles through a nanofilter or molecular sieve having a pore size less than 100 nm before depositing in the reservoir, and returning collected cannabinoid nanoparticles larger than 100 nm in a return stream to the cryogenic cannabinoid stream.

Any of the preferred embodiments herein may include a process wherein the impact surface is a metal surface at low temperature.

Any of the preferred embodiments herein may include a process wherein the impact surface is a second nozzle delivering a second cryogenic cannabinoid stream under high speed to the collision chamber to collide the cryogenic cannabinoid stream with the second cryogenic cannabinoid stream to obtain cannabinoid nanoparticles.

Any of the preferred embodiments herein may include a process wherein the cannabis concentrate from hemp having less than 0.3% THC is selected from the group consisting of: cannabis oil, hash oil, cannabis distillate, cannabis isolate, Cannabis flower essential oil, kief, hash, cannabis resin, cannabis wax, cannabis tincture, and mixtures or combinations containing the same.

Any of the preferred embodiments herein may include a process wherein the surfactant is selected from the group consisting of a nonionic surfactant, cationic surfactant, anionic surfactant, amphoteric surfactant, and a mixture or combination thereof.

Any of the preferred embodiments herein may include a process wherein the solvent is selected from the group consisting of water, ethanol, butane, propane, hexane, petroleum ether, methyl tertbutyl ether, diethyl ether, carbon dioxide ($CO_2$), olive oil, and a mixture or combination thereof.

Any of the preferred embodiments herein may include a process wherein the homogenizer is selected from the group consisting of a rotor-stator homogenizer, a bead mill homogenizer, a pressure homogenizer, an ultrasonic homogenizer, and a piston homogenizer.

Any of the preferred embodiments herein may include a composition made by the process provided herein.

Any of the preferred embodiments herein may include a composition formulated into a suspension, an emulsion, or a mixture.

In a preferred embodiment, the invention utilizes the cannabinoid nanoparticles to manufacture cannabinoid-containing products. In a preferred embodiment, the cannabinoid-containing products are made using nanosuspensions, and nanoemulsions.

In a preferred embodiment, the invention provides a process for centrifugal distillation of cannabinoid-containing oil, comprising: Obtaining a cannabis concentrate, extract, or isolate, "cannabinoid-containing oil" from hemp having less than 0.3% THC; Distilling the cannabinoid-containing oil using a novel centrifugal distillation system that comprises a low pressure chamber having disposed therein a stationary outer condenser/collector with a rotating inner distiller unit having a rotating heated disk surface, wherein the cannabinoid-containing oil is introduced into the center of the rotating heated disk surface and migrates by centrifugal force as a thin film across the top surface of the rotating heated disk surface towards an adjacent condenser element, wherein more volatile fractions evaporate more rapidly and will either evaporate and condense or roll off the rotating heated disk surface and be recirculated into the liquid cannabinoid-containing oil for additional centrifugal distillation.

In a preferred embodiment, the invention utilizes the centrifugal distillation to obtain purified cannabinoid distillates and/or fractions. In a preferred embodiment, the purified cannabinoid distillates and/or fractions are further processed using a cryogenic nanoparticle process to manufacture cannabinoid-distillate nanoparticles, and products containing the same.

Any of the preferred embodiments herein may also include wherein the cannabinoid nanoparticles are dried using low-frequency sonication drying, the dried cannabinoid nanoparticles mixture is allowed to freeze overnight and then placed in a funnel connected to a feeder attached to a jet mill, the cryogenic carrier fluid is a liquid and gas nitrogen mixture adjusted to a flow of 100 to 180 CFM (80 to 100 psi combined input pressure) and a temperature of −2 Celsius above a cyclone read from a flowmeter, the dried cannabinoid nanoparticles mixture is fed into the jet mill over 5 minutes and the resulting powder in a jet mill cup below a jet mill cyclone is passed again through the mill three additional passes, the resulting jet-milled dried cannabinoid nanoparticles powder having a diameter less than 10 microns.

Any of the preferred embodiments herein may also include wherein the cannabinoid nanoparticles are Spray-dried cannabinoid nanoparticles are mixed with inhalation-grade excipients in a mixer at room temperature for 10 minutes, the resulting dry mix is then granulated in a shear mixer with water, the wet granulation is then spread into a stainless steel bowl and dried, the dried granules are then milled through a mesh (1 mm) screen, the mixture is allowed to freeze overnight and jet milled over 5 minutes and the resulting powder in the cup below the cyclone passed again through the mill three additional passes, the resulting jet-milled dried cannabinoid nanoparticles powder having a diameter less than 10 microns.

Any of the preferred embodiments herein may also include wherein the cannabinoid nanoparticles are mixed with excipients in a mixer at room temperature for 10 minutes, the mixture is placed in a funnel connected to a spoon feeder attached to a jet mill, the jet mill liquid and gas nitrogen mixture is adjusted resulting in a pressure of 90 psi (+/−10 psi) in each jet, the powder is fed into the mill over approximately 5 minutes and the resulting powder in the cup below the cyclone passed again through the mill for additional passes, the resulting jet-milled dried cannabinoid nanoparticles powder having a diameter less than 10 microns, and the particles optionally added to a heated propylene glycol/aqueous solution in preparation of a clear hydrogel.

Any of the preferred embodiments herein may also include wherein the cannabinoid nanoparticles are mixed with excipients in a 1 kg batch and jet milled.

Any of the preferred embodiments herein may also include wherein the cannabinoid nanoparticles are mixed with excipients in a 1 kg batch and jet milled, the powders are recovered at >98% each pass and the particle size after each pass has a range 2250 nm-190 nm (Pass 1), 524 nm-44 nm (Pass 2), 400 nm-33 nm (Pass 3), and 264 nm-51 nm (Pass 4), the Cannabinoid nanoparticle formulations are developed using milled powder from Pass 4.

Any of the preferred embodiments herein may also include wherein the cannabinoid nanoparticles are mixed with 4% PVP K-30 and jet milled in 20 kg batches, the cannabinoid nanoparticle powders are recovered at >75% and the particle size ranges from 652 nm-98 nm by Coulter.

Any of the preferred embodiments herein may also include wherein the cannabinoid nanoparticles are mixed with 95% methacrylic acid copolymer (Eudragit L100, Rohm) in a 20 kg batch, and dried using a 20% chloroform/80% isopropanol solution in a stainless steel container overnight, the cannabinoid nanoparticles are jet milled in one or more passes, the Cannabinoid nanoparticles with a diameter from 50 microns and smaller.

Any of the preferred embodiments herein may also include wherein the cannabinoid nanoparticles are formulated in an oral taste-masked formulation.

Any of the preferred embodiments herein may also include wherein the cannabinoid nanoparticles are loaded into liposomes to produce a cannabinoid nanoparticle liposome product.

Any of the preferred embodiments herein may also include wherein the cannabinoid nanoparticle liposome is selected from one of the following: a 50-100 nm Cannabinoid Nanoparticle Liposome product manufactured through evaporating fully hydrogenated soy phosphatidylcholine (HSPC), distearoylphosphatidylglycerol (DSPG), Cholesterol from dichloromethane, hydration with lactose solution, size reduction by homogenization, filtration, and lyophilization; a <100 nm Cannabinoid Nanoparticle Liposome product manufactured through evaporating egg phosphatidylcholine (EPC) and dimyristoylphosphatidylcholine (DMPC) from dichloromethane, hydration with lactose solution, size reduction by homogenization, filtration, and lyophilization; a 50-100 nm Cannabinoid Nanoparticle Liposome product manufactured through evaporating dioleoyl phosphatidylcholine (DOPC) and Cholesterol from dichloromethane, hydration with lactose solution, size reduction by homogenization, filtration, and lyophilization; a 100 nm Cannabinoid Nanoparticle Liposome product manufactured through evaporating fully hydrogenated soy phosphatidylcholine (HSPC), N-(carbonyl-methoxy-polyethlyeneglycol-2000)-distearolyphosphatidylethanolamine (MPEG-2000-DSPE) and Cholesterol from dichloromethane, hydration with aqueous solution, size reduction by homogenization, filtration, and lyophilization; a 45-80 nm Cannabinoid Nanoparticle Liposome product manufactured through evaporating distearoyl-phosphatidylcholine (DSPC) and Cholesterol from dichloromethane, hydration with aqueous solution, size reduction by homogenization, filtration, and lyophilization; and a 110 nm Cannabinoid Nanoparticle Liposome product manufactured through evaporating distearoylphosphatidylcholine (DSPC), N-(carbonyl-methoxy-polyethlyeneglycol-2000)-distearolyphosphatidylethanolamine (MPEG-2000-

DSPE) and Cholesterol from dichloromethane, hydration with aqueous solution, size reduction by homogenization, filtration, and lyophilization.

Any of the preferred embodiments herein may also include wherein the cannabinoid nanoparticle liposome is selected from one of the following: a 20 nm Cannabinoid Nanoparticle Liposome product manufactured through a double-emulsification method, using dioleoyl phosphatidyl-choline (DOPC), dipalmitoylphosphatidylglycerol (DPPG), Cholesterol, and triolein, to obtain 20 nm cannabinoid nanoparticle MLV liposomes; a 24-31 nm Cannabinoid Nanoparticle Liposome product manufactured through a double-emulsification method, using dierucoyl phosphati-dylcholine (DEPC), dipalmitoylphosphatidylglycerol (DPPG), Cholesterol, and tricaprylin, to obtain 24-31 nm cannabinoid nanoparticle MLV liposomes; and a 17-23 nm Cannabinoid Nanoparticle Liposome product manufactured through a double-emulsification method, using dioleoyl phosphatidylcholine (DOPC), dipalmitoylphosphatidylglyc-erol (DPPG), Cholesterol, triolein, and tricaprylin to obtain 17-23 nm cannabinoid nanoparticle MLV liposomes.

Any of the preferred embodiments herein may also include wherein the cannabinoid nanoparticle liposome is selected from one of the following: a 200-300 nm Cannabi-noid Nanoparticle Liposome product manufactured through a double-emulsification method, using dipalmitoyl phospha-tidylcholine (DPPC), and Cholesterol, and an ethanol infu-sion to minimize the amount of lipids-ethanol solution and the cannabinoid nanoparticles are mixed by a Y-connector and in-line mixer to form 200-300 nm cannabinoid nanopar-ticle liposomes.

Any of the preferred embodiments herein may also include wherein the cannabinoid nanoparticle is encapsu-lated in an infusible polymer shell to obtain a dry, free flowing encapsulated cannabinoid product having high uni-formity of thickness, the infusible polymer shell comprising an aqueous encapsulant selected from lactose, sodium alg-inate, agarose, gelatin, or pectin, the encapsulated cannabi-noid nanoparticle is cold-pressed, dried, and the dried mate-rial is milled to an encapsulated cannabinoid nanoparticle powder.

Any of the preferred embodiments herein may also include wherein the cannabinoid nanoparticle is formulated with an emulsifier as a nano-emulsion.

Definitions

The terminology used herein is for the purpose of describ-ing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "includ-ing" should be interpreted as "including but not limited to," the term "having" should be interpreted as "having at least," etc.). Similarly, the terms "comprises" and/or "comprising," when used in this specification, specify the presence of stated features, integers (or fractions thereof), steps, opera-tions, elements, and/or components, but do not preclude the presence or addition of one or more other features, integers (or fractions thereof), steps, operations, elements, compo-nents, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The term "cannabinoid-containing oil" refers broadly to any cannabis oil, and includes cannabis extract oil, CBD oil, and any oil containing cannabinoids. The cannabinoids and/or oil are preferably extracted from federally compliant hemp having less than 0.3% delta-9-THC.

The term "CBD" refers to cannabidiol and has a molecu-lar weight of 314.47 g/mol.

The term "CBD Distillate" refers to the process of apply-ing high heat (boiling point) to raw extracted oil in a distillation chamber to separate the oil components and obtain highly pure CBD. CBD distillate does not contain or contains only a very small percentage of terpenes.

The term "CBD Isolate" refers to 99% pure CBD created by cooling and crystallizing CBD extract to form a white powder The term "cannabinoid" or "cannabinoids" as used herein encompasses at least the following substances: Δ-8 tetrahy-drocannabinol, Δ-9-tetrahydrocannabinol (THC), cannabi-nol (CBN), cannabidiol (CBD), cannabigerol (CBG), Δ-9 (11)-tetrahydrocannabinol (exo-THC), cannabichromene (CBC), tetrahydrocannabinol-C3 (THC-C3), tetrahydrocan-nabinolˆ (THC-C4).

Examples of cannabinoids include: tetrahydrocannabino-lic acid (THCA), tetrahydrocannabinol (THC), delta-8-tet-rahydrocannabinol (delta-9-THC), delta-8-tetrahydrocan-nabinol (delta-8-THC), cannabidiolic acid 9CBDA), cannabidiol (CBD), tetrahydrocannabivarin (THCV), can-nabigerolic acid (CBGA), cannabigerol (CBG), cannabino-lic acid (CBNA), cannabino (CBN)l, cannbichromenic acid (CBCA), cannabichromene (CBC), cannabicyclolic acid (CBLA), and cannabicyclol (CBL).

The term "*Cannabis*" refers to a plant that belongs to a family (Cannabaceae) with a single genus (*Cannabis*) with only one species (*sativa*) that has many varieties. The plant is very rich in constituents, the most specific of which are the cannabinoids that have not been reported in any other plants and it has a broad pharmacological properties with tremen-dous medical potential in the treatment of epilepsy, spastic-ity, inflammation, irritable bowel syndrome, pain and other disorders. Methods for growing, harvesting, processing, formulation, and use continue to evolve towards an important position in the pharmacopeia. *Cannabis* (hemp) belongs together with the genus *Humulus* (hop) to the family of Cannabaceae, wherein however *Humulus* does not contain cannabinoids. Within the genus *Cannabis* there is a botanical distinction made, more specifically in the *Cannabis* species *Cannabis sativa* Linnaeus, *Cannabis* indica LAM, and *Cannabis ruderalis* or in the "species complex" *Cannabis sativa* L., consisting of the *Cannabis sativa* subgroups ssp. *sativa* and ssp. *indica*. In addition, cannabis can be distinguished into a drug hemp and fiber hemp, wherein the distinction is made on the basis of the ratio of the primary cannabinoids which are cannabidiol (CBD) and Δ9-tetrahydrocannabinol (Δ9-THC or delta 9 THC). Hemp which is dried and extracted for this purpose may have at most a Δ9-THC content of 0.3% on a dry weight basis, *Cannabis sativa* L. contains more than 400 different ingredients, including more than 60 compounds from the class of cannabinoids. Hemp is a strain of the *Cannabis sativa* plant that is grown specifically for the extraction of cannabinoids. Additionally, another form of *Cannabis* plant, wherein the plant may be *Cannabis Sativa* or *Cannabis Indica*, may be present and extracted from marijuana and thus contain a higher amount of THC or Δ9-tetrahydrocannabinol while containing other cannabinoids such as CBD and other forms of cannabinoids.

The term "cannabinoids", as used herein, refers in a non-limiting sense to:

Cannabigerol types (CBG): cannabigerol ((E)-CBG-C5), cannabigerol monomethylether ((E)-CBGM-C5 A), cannabinerolic acid A ((Z)-CBGA-C5 A), cannabigerovarin ((E)-CBGV-C3), cannabigerolic acid A ((E)-CBGA-C5 A), cannabigerolic acid A monomethylether ((E)-CBGAM-C5 A), cannabigerovarinic acid A ((E)-CBGVA-C3 A);

Cannabichromene types (CBC): cannabichromene (CEO-C5), cannabichromenic acid A (CBCA-C5 A), cannabichromevarin (CBCV-C3), cannabichromevarinic acid A (CBCVA-C3 A);

Cannabidiol types (CBD): cannabidiol (CEO-C5), cannabidiol monomethylether (CBDM-C5), cannabidiol-C4 (CBD-C4), cannabidivarin (CBDV-C3), cannabidiorcol (CEO-C1), cannabidiolic acid (CBDA-C5), cannabidivarinic acid (CBDVA-C3);

Cannabinodiol types (CBND): cannabinodiol (CBND-C5), cannabinodivarin (CBND-C3);

Tetrahydrocannabinol types (THC): Δ9-tetrahydrocannabinol (Δ9-THC-C5 or delta 9 THC), Δ9-tetrahydrocannabinol-C4 (Δ9-THC-C4), Δ9-tetrahydrocannabivarin (Δ9-THCV-C3), Δ9-tetrahydrocannabiorcol (Δ9-THCO-C1), Δ9-tetrahydrocannabinolic acid (Δ9-THCA-C5 A), Δ9-tetrahydrocannabinolic acid B (Δ9-THCA-C5 B), Δ9-tetrahydrocannabinolic acid-C4 (Δ9-THCA-C4 A and/or B), Δ9-tetrahydrocannabivarinic acid A (Δ9-THCVA-C3 A), Δ9-tetrahydrocannabiorcolic acid (Δ9-THCOA-C1 A and/or B), (−)-Δ8-trans-(6aR,10aR)-Δ8-tetrahydrocannabinol (Δ8-THC-C5), (−)-Δ8-trans-(6aR,10aR)-tetrahydrocannabinolic acid A (Δ8-THCA-C5 A); (−)-(6aS,10aR)-Δ9-tetrahydrocannabinol ((−)-cis-Δ9-THC-C5);

Cannabinol types (CBN): cannabinol CBN-C5, cannabinol-C4 (CBN-C4), cannabivarin (CBN-C3), cannabinol-C2 (CBN-C2), cannabiorcol (CBN-C1), cannabinolic acid A (CBNA-C5 A), cannabinolmethylether (CBNM-C5)

Cannabitriol types (CBT): (−)-(9R,10R)-trans-cannabitriol ((−)-trans-CBT-C5), (+)-(9S,10S)-cannabitriol ((+)-trans-CBT-05), (±)-(9R,10S/9S,10R)-cannabitriol ((±)-cis-CBT-C5), (−)-(9R,10R)-trans[10-O-ethyl-cannabitriol]((−)-trans-CBT-OEt-C5), (±)-(9R,10R/9S,10S)-cannabitriol-C3 ((±)-trans-CBT-C3), 8,9-dihydroxy-Δ6a(10a) tetrahydrocannabinol (8,9-Di-OH-CBT-C5), cannabidiolic acid A (CBDA-C5 9-OH-CBT-C5 ester), (−)-(6aR,9S,10S,10aR)-9,10-dihydroxy-hexahydrocannabinol, cannabiripsol cannabiripsol-C5, (−)-6a,7,10a-trihydroxy-Δ9-tetrahydrocannabinol ((−)-cannabitetrol), 10-Oxo-Δ6a(10a) tetrahydrocannabinol (OTHC);

Cannabielsoin types (CBE): (5aS,6S,9R,9aR)-C5-cannabielsoin (CBE-C5), (5aS,6S,9R,9aR)-C3-cannabielsoin (CBE-C3), (5aS,6S,9R,9aR)-cannabielsoic acid A (CBEA-C5 A), (5aS,6S,9R,9aR)-cannabielsoic acid B (CBEA-C5 B), (5aS,6S,9R,9aR)-C3-cannabielsoic acid B (CBEA-C3 B), cannabiglendol-C3 (OH-iso-HHCV-C3), dehydrocannabifuran (DCBF-C5), cannabifuran (CBF-C5);

Isocannabinoids: (−)-Δ7-trans-(1R,3R,6R)-isotetrahydrocannabinol, (±)-Δ7-1,2-cis-(1R,3R,6S/1S,3S,6R)-isotetrahydrocannabivarin, (−)-Δ7-trans-(1R,3R,6R)-isotetrahydrocannabivarin;

Cannabicyclol types (CBL): (±)-(1aS,3aR,8bR,8cR)-cannabicyclol (CBL-C5), (1)-(1aS,3aR,8bR,8cR)-cannabicyclolic acid A (CBLA-C5 A), (±)-(1aS,3aR,8bR,8cR)-cannabicyclovarin (CBLV-C3);

Cannabicitran types (CBT): cannabicitran (CBT-C5);

Cannabichramanon types (CBCN): carmabichromanon (CBCN-C5), Cannabichromanon-C3 (CBCN-C3) cannabcoumaronon (CBCON-C5)

The term "carboxylic acids of cannabinoids", as used herein, refers in a non-limiting sense to the carboxylic acids of cannabinoids that are found in the crude oil. These carboxylic acids are biosynthetic precursors.

The term "$CO_2$ extraction", as used herein, refers in a non-limiting sense to a process for obtaining CBD from industrial hemp that comprises by way of illustration in a non-limiting example the following steps: —extraction with supercritical $CO_2$ (e.g. 60° C., 250 bar); —decarboxylation (e.g. 80° C., 2 hours); and—separation in a high pressure column (using $CO_2$ as solvent). The method is shown to yield an extract containing CBD in approximately 90% purity.

The term "distillate" or "cannabis distillate" as used herein, refers in a non-limiting sense to a product made from distillation that contains one or more cannabinoid compounds.

The term "Distillation", as used herein, refers in a non-limiting sense to using heat and condensation upon cannabis oil to separate substances having different boiling points. As used herein, the temperature used in the centrifugal distillation process may range and include 50 to 350 degrees Celsius, and preferably 75 to 250 degrees Celsius, and more preferably 100 to 200 degrees Celsius.

The term "dosage form", as used herein, refers in a non-limiting sense to cannabinoid nanoparticle beverage formulations that include gels, powders, suspensions, emulsions, concentrates, slurries, and liposomal and encapsulated forms.

The term "encapsulation", as used herein, refers in a non-limiting sense to a process or mechanism used to provide a protective shell or a membrane barrier or a coating or a substance that contains another substance or a composition that wraps around another composition or other meaning that extends to the current definition of encapsulation in its broadest meaning or interpretation. Nano-encapsulation is the process of encapsulating a substance with various coating materials at the nanoscale range from 50 to 1000 nm in size and preferably from 100 to 500 nm in size. As a result, the cannabinoid or mixture of cannabinoids may be nano-encapsulated to produce a particle size in the nanoscale range of 50 to 1000 nm in size and preferably from 100 to 500 nm.

The terms "extract" or "extraction", as used herein, refer in a non-limiting sense to a process for obtaining raw Cannabinoid extract from dried Hemp plant material. Non-limiting illustrative processes include supercritical $CO_2$ extraction, liquid chromatography, solvent extraction, distillation extraction, and olive oil extraction. Extracts contain other plant components—major and minor cannabinoids, terpenes, and flavonoids—that isolates do not. The distillation method uses alcohols, such as ethanol, to extract the cannabinoids from the marijuana or hemp plant. The extract that results from this distillation can be referred to as cannabinoid-containing extract or THC, or THC oil, or THC Distillate or CBD or CBD oil or CBD Distillate or any of the cannabinoids listed above. In another method, hydrocarbon extraction using hydrocarbon solvents such as butane, pentane, propane, hexane, or heptane has also been used to extract cannabinoids from the dried marijuana or hemp. Yet in another method lipid extraction such as coconut oil can be used to extract cannabinoids from the marijuana or hemp.

The term "hemp" does not include marijuana. "Natural hemp", "industrial hemp", or "hemp" as used herein refers to a variety of *Cannabis sativa* that is federally compliant with the Farm Bill and contains less than 0.3% Delta-9-tetrahydrocannabinol (THC). Important commercial benefits include that industrial hemp cultivars grow approximately twice a fast as marijuana, processes that extract CBD from industrial hemp obtain a cleaner CBD that can be directly chemically converted in one-step to valuable cannabinoids, and the cost for industrial hemp products is about one tenth of the cost of marijuana originated products.

The term "isolate", as used herein, refers in a non-limiting sense to a cannabinoid crystalline powder. An example is CBD Isolate, which is one of the purest form of cannabidiol, and unlike the oil, Isolates contain no THC or practically no other plant impurities. CBD Isolate may be 99% pure cannabidiol or even higher purity depending on the extraction procedure. Furthermore, the cannabinoid or cannabinoid mixture may contain other cannabis compounds such as flavonoids and terpenes.

The term "Kief", as used herein, refers in a non-limiting sense to a high potency THC composition consisting of accumulated trichomes, or resin glands, sifted from cannabis flowers through a mesh screen or sieve. Trichomes are the crystal-like hairs that cover the cannabis flower bud. Trichomes secrete a sticky resin containing the terpenes and cannabinoids that give cannabis its unique qualities. As concentrated resin glands, kief occurs as a fine powder and is a potent form of cannabis. More simply, Kief is a cannabis concentrate that contains from about 50%-80% THC and includes both cannabinoids and terpenes.

The term "liposome" as used herein refers to self-assembled (phospho)lipid-based drug vesicles that form a bilayer (uni-lamellar) and/or a concentric series of multiple bilayers (multilamellar) enclosing a central aqueous compartment. The size of liposomes ranges from 30 nm to 1000 nm scale, with the phospholipidbilayer being 4-5 nm thick. Liposomes herein are used as a delivery vehicle for the cannabinoid nanoparticles, nanoparticle suspensions, or nanoparticle emulsions. Liposomes may be administered via parenteral, pulmonary, oral, transdermal, ophthalmic, and nasal routes. Commercially approved liposomes have a composition made from two to five of the following ingredients: fully hydrogenated soy phosphatidylcholine (HSPC), egg phosphatidylcholine (EPC), distearoylphosphatidylcholine (DSPC), dioleoyl phosphatidylcholine (DOPC), dierucoyl phosphatidylcholine (DEPC), palmitoyl-2-oleoyl-sn-glycero-3-phosphocholine (POPC), dipalmitoyl phosphatidylcholine (DPPC), dimyristoylphosphatidylcholine (DMPC), dipalmitoylphosphatidylglycerol (DPPG), distearoylphosphatidylglycerol (DSPG), dioleoyl phosphatidylserine (DOPS), dioleoylphosphatidylserine (OOPS), cholesterol (Chol), sphingomyelin (SM), N-(carbonyl-methoxypolyethlyeneglycol-2000)-distearolyphosphatidy-lethanolamine (MPEG-2000-DSPE). Manufacturing processes for liposomes include the thin-film hydration method, the ethanol injection method, and the double emulsion method. The processes for preparing drug (cannabinoid nanoparticle) loaded liposomes include (1) the preparation of MHLVs or ULVs depending on the choice of methods; (2) size reduction if necessary; (3) preparation of the drug solution(s) and drug loading, while this step is combined with step 1 in the case of passive drug loading; (4) buffer exchange and concentration if necessary; (5) sterile filtration or aseptic processing; (6) lyophilization, if needed, and packaging.

The term "lyophilized sphere or particle", as used herein, refers in a non-limiting sense to a cannabinoid distillate formulated as a nanoparticle having a diameter of about 50 to 1000 nanometers and preferably 100 to 500 nm and having a shell comprising a biodegradable polymer containing a cannabinoid or mixture of cannabinoids. As used herein, the term "sphere" is not intended to suggest uniformity in shape, or geometric form. The spheres may have irregularities and be particle-like. The terms sphere and particle are used interchangeably. The term shell is used to denote the outer surface of the sphere or particle.

The term "molecular sieve", as used herein, refers in a non-limiting sense to a material with pores of uniform size. These pore diameters are similar in size to small molecules, and thus large molecules cannot enter or be adsorbed, while smaller molecules can. As a mixture of molecules migrates through the stationary bed of porous, semi-solid substance referred to as a sieve (or matrix), the components of the highest molecular weight (which are unable to pass into the molecular pores) leave the bed first, followed by successively smaller molecules. Some molecular sieves are used in size-exclusion chromatography, a separation technique that sorts molecules based on their size. Another important use is as a desiccant. Molecular sieves contemplated herein include aluminosilicate zeolites, Si/Al with molar ratio less than 2, sodium aluminosilicate as specifically approved by the U.S. FDA for use with consumable products under 21 CFR 182.2727, zeolites, activated charcoal, silica gel/silicon dioxide for 20-50 nm, macroporous silica for 20-100 nm, porous glass, and compositions providing the same or similar function, the same or similar way, with the same or similar results.

The pore diameter of a molecular sieve is measured in ångströms (Å) or nanometres (nm). According to IUPAC notation, microporous materials have pore diameters of less than 2 nm (20 Å) and macroporous materials have pore diameters of greater than 50 nm (500 Å); the mesoporous category thus lies in the middle with pore diameters between 2 and 50 nm (20-500 Å).

The term "nanoparticle", as used herein, refers in a non-limiting sense to a small particle that ranges on average between 50 to 1000 nm in size, wherein the majority of the particles are made up of such a wide range of size in its composition. Some of these nanoparticles may be independent in size and some may be aggregated or agglomerated or attached into a much larger particle that can later be redistributed upon mixing or shaking or simply dissociated over time. Some nanoparticles could be made up of only a few hundred atoms and have much smaller sizes and still be considered to be nanoparticles in this invention, however, a substantial amount of the nanoparticle will be in the preferred size ranges of 50 to 100 nm, 50 to 250 nm, 50 to 500 nm, 100 to 250 nm, 100 to 500 nm, and 250 to 500 nm.

The term "nanosuspension", as used herein, refers in a non-limiting sense to the process or mechanism in which nanoparticles of a substance are dispersed but not totally dissolved in a fluid. A nanosuspension is defined as a heterogeneous mixture in which the solid nanoparticles are spread throughout the liquid without dissolving in it or without dissolving entirely in it. A nano-suspension is a submicron colloidal dispersion of discrete nanoparticles, which are dispersed throughout the solution. Cannabinoid nano-suspension could be a dispersion of cannabinoid nanoparticles which are dispersed throughout the solution. Nano-suspensions offer a means of administering increased concentration of poorly soluble drugs or substances and possibly enhancing the bioavailability of the formulation when consumed or ingested in mammals and preferably in humans. Nano-suspensions of cannabinoid nanoparticles or mixture of cannabinoid nanoparticles as beverages are applied to delivering said cannabinoid composition via oral delivery routes.

The term "nanoencapsulation" as used herein refers in a non-limiting sense to a method to produce nano-encapsulated substance having a shell of insoluble, infusible, high molecular weight condensation polymer. The nano-encapsulating process of cannabinoid nanoparticles comprises division and dispersion of the substance to be encapsulated as a discontinuous phase, within a continuous fluid phase. Each phase must contain an intermediate or an intermediate must be added, which will react with the intermediate in the other phase to form a continuous high molecular weight condensation polymer film at the interface of the two phases. The dispersed cannabinoid or mixture of cannabinoids is enclosed within the polymer film.

Nano-encapsulation of isomers of tetrahydrocannabinol (THC) maintains a reactive material in an inert stage until such time as it is called upon to perform a given function. Thus, inertness is provided by interposing, by encapsulation, a non-reactive barrier or shell between the reactive material and its immediate surrounding. Removal of the barrier or shell by any suitable means activates the encapsulated cannabinoids that are present in the cannabinoid nano-suspension. In this manner, the handling properties of solids can be conferred on liquids and gases. The nano-encapsulated cannabinoid composition is maintained inactive until the shell is ruptured by pressure of a stylus or other means.

The term "nano-suspension" as used herein refers in a non-limiting sense to a cannabinoid nanoparticle as an active ingredient that is coated with a suitable protective layer and when the cannabinoid is taken internally, has a delayed affect or sustained release affect or extended release affect but remains inactive until the polymer layer is dissolved. As is apparent, depending on the encapsulating shell present in the cannabinoid nano-suspension, the influence of the drug can be delayed from a matter of minutes up to several hours or released even more rapidly with faster therapeutic benefits.

Although several methods are presently known for nano-encapsulation of cannabinoids, such as the nano-encapsulation of a THC oil with a lipid shell utilizing a coacervation process. The prior processes are focused on THC extracted from marijuana and further purified with various technologies used in the market today, but the prior processes exclude nano-encapsulation of cannabinoid nanoparticle or mixture of cannabinoid nanoparticles that are purified via molecular distillation to a higher level of purity. Furthermore, the existing suspension-evaporation method used for nano-encapsulation of THC is limited in scope to specific procedures of extraction and separation and purification and further steps to produce a cannabinoid nanoparticle of 50 to 1000 nm in size to preferably 100 to 500 nm in size.

The term "vacuum", as used herein, refers in a non-limiting sense to the low pressure distillation conditions used in the centrifugal distillation process described herein.

The term "Winterization", as used herein, refers in a non-limiting sense to combining extracted CBD oil with ethanol and freezing overnight, which is then filtered to remove fats and other impurities, and the filtrate is heated to evaporate the ethanol.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

FIGURES

Referring now to the FIGURES, FIG. 1 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles as a powder or slurry.

FIG. 2 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles as a powder or slurry.

FIG. 3 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and splitting to obtain two or more cryogenic cannabinoid streams, and delivering each of the two or more cryogenic cannabinoid streams under high speed to a separate nozzle within a collision chamber to collide the streams with each other to obtain cannabinoid nanoparticles as a powder or slurry.

Figure 4:
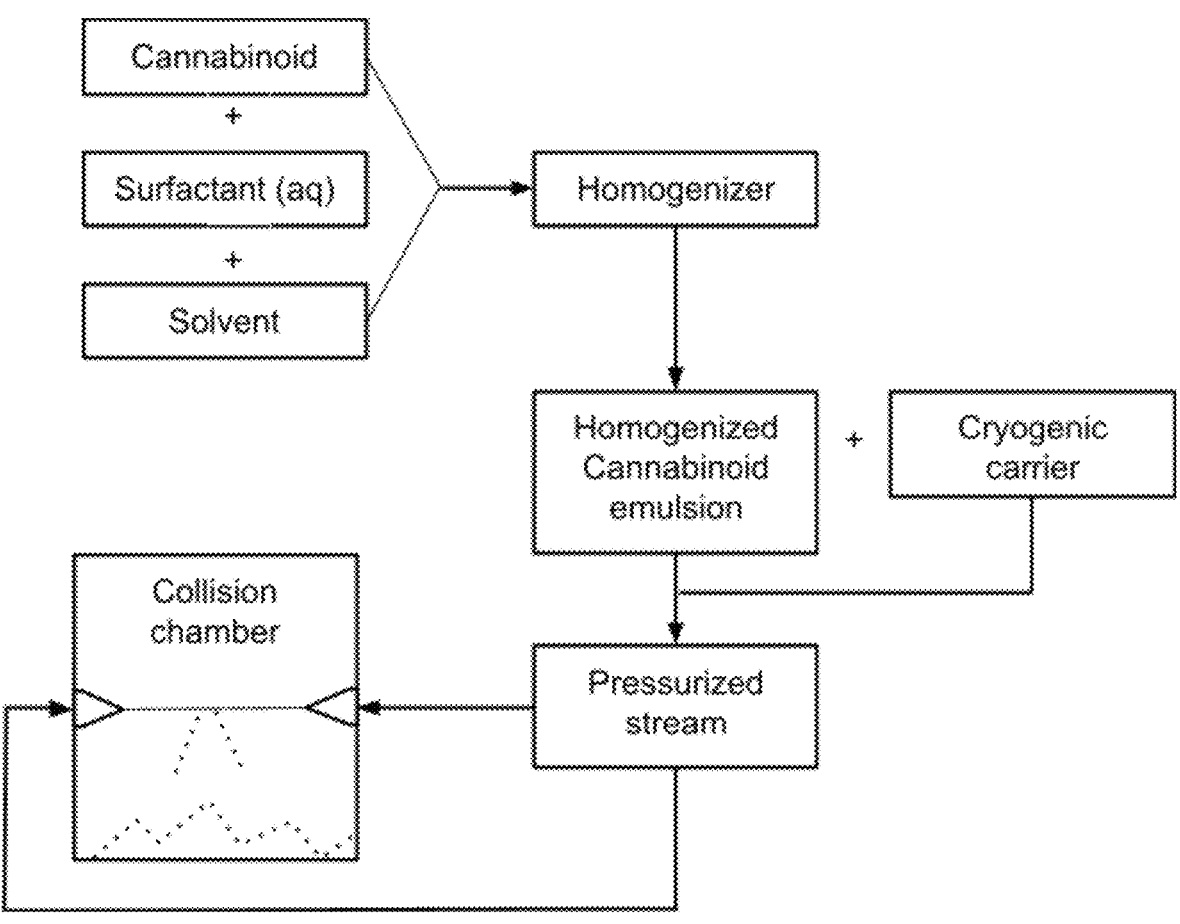
FIG. 4 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and splitting to obtain two or more cryogenic cannabinoid streams, and delivering each of the two or more cryogenic cannabinoid streams under high speed to a separate nozzle within a collision chamber to collide the streams with each other to obtain cannabinoid nanoparticles.

FIG. 4 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and splitting to obtain two or more cryogenic cannabinoid streams, and delivering each of the two or more cryogenic cannabinoid streams under high speed to a separate nozzle within a collision chamber to collide the streams with each other to obtain cannabinoid nanoparticles as a powder or slurry.

FIG. 5 is a flowchart illustrating in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles as a powder or slurry.

Figure 6:
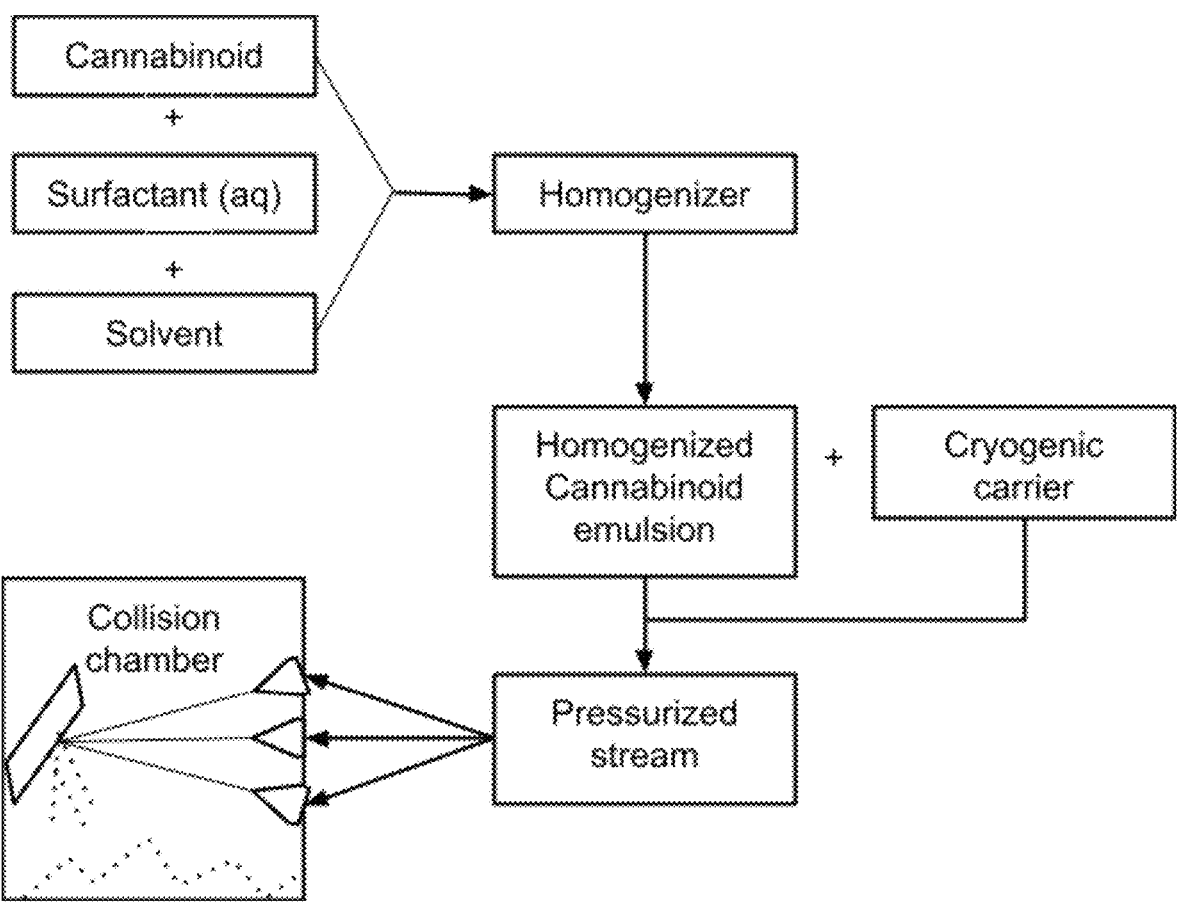
FIG. 6 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles.

FIG. 6 is a graphic illustration that shows in a non-limiting preferred embodiment the process of Mixing a cannabis concentrate from hemp having less than 0.3% THC with aqueous surfactant and solvent to obtain a cannabinoid emulsion, and homogenizing the cannabinoid emulsion in a homogenizer to obtain a homogenized cannabinoid emulsion; and Mixing the homogenized cannabinoid emulsion with a cryogenic carrier under pressure and to obtain a cryogenic cannabinoid streams, and delivering the cryogenic cannabinoid streams under high speed to a nozzle within a collision chamber to collide the stream with an impact surface to obtain cannabinoid nanoparticles as a powder or slurry.

Figure 7:
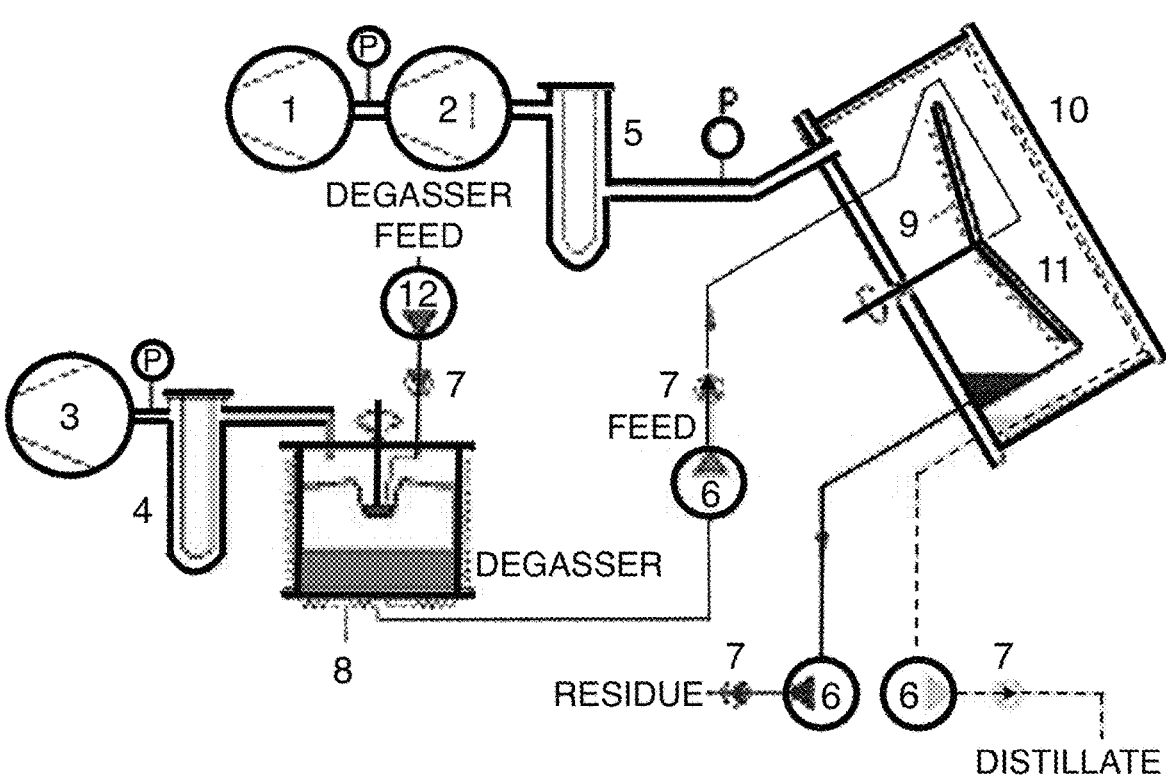
FIG. 7 is a graphic illustration that shows a non-limiting embodiment of a molecular/centrifugal distillation apparatus.

FIG. 7 is a graphic illustration that shows a non-limiting embodiment of a molecular/centrifugal distillation apparatus. The Centrifugal Distillation System (Pilot 15, from Myers) utilizes thermal separation process in order to obtain vaporizable liquids from a gas phase and to separate substances that are difficult to vaporize, wherein a cannabinoid containing extract is enriched in the distillate. This molecular distillation unit is designed to distill materials in the pressure range from 700×10-3 Torr down to 1×10-3 Torr. The lower the pressure, the lower the heat required to effect distillation. The lower the heat, the lower the chance of damaging the product and reduces the energy costs required for the purification process. The molecular distillation unit has a complete vacuum system as can be seen from the diagram. Both the degasser and the high vacuum distillation chamber have vapor traps; these vapor traps are cooled by liquid Nitrogen or equitant medium. A diffusion-ejector pump and a rotary vane vacuum pump evacuate the main chamber. The degasser has a separate rotary vane vacuum pump. There are three regions of pressure monitoring. This enables the operator to get accurate pressure measurements in the three critical areas: the degasser, the high-vacuum chamber, and the fore line.

Centrifugal Distillation

The molecular centrifugal distillation unit is designed as a continuous flow, vacuum distillation system. The diagram in FIG. 7 illustrates the flow of material through the still. The raw cannabinoid oil substrate is pumped from the supply/feed tank by a variable speed feed pump (12) into the degasser. In the degasser small amounts of low boiling materials such as any volatiles that may be incorporated into the cannabinoid mixture and trapped gases are removed to enable more efficient vacuum distillation at the next stage.

Referring now to graphical illustration FIG. 7 and flowchart FIG. 8 to describe the process of using the centrifugal distillation system, a feed pump (6) moves the degassed material onto the center of a heated, spinning Rotor (11) in the high vacuum distillation chamber (10). On the Rotor the cannabinoid or mixture of cannabinoids spread out into a thin film. As the cannabinoid spreads across the Rotor, a certain portion (the distillate) evaporates. The cannabinoid fraction which distills is selected by the operator by adjusting the temperature. Once set, this remains constant until the production run is completed or until new conditions are selected.

The distillate cannabinoid vapor condenses in the vacuum chamber on a water-cooled condenser in Chamber (10) and moves to a separate liquid transfer pump and is removed from the system through check valve to atmosphere. The raw cannabinoid oil portion which does not distill, (the residue) flows off the edge of the rotor to be contained by a separate gutter and moves to another liquid transfer pump through a check valve to atmosphere.

Depending upon the raw cannabinoid oil material or process requirements, either the distillate or the residue may be your final product. In many cases both cannabinoid fractions may be of value.

Processing

As described in FIG. 7 and FIG. 8, the product path through the molecular centrifugal distillation unit is heated in separate zones. The zones can be temperature regulated for conditioning of the product for various steps in the process. They are the degasser feed line, the degasser wall, the rotor feed line, rotor heater temperature, distillate line and residue line. The control center offers displays of the three vacuum stations, the actual and set point temperatures of the degasser pre-heater, degasser heater, the rotor pre-heater, the rotor heater, residue line heater and distillate line heater. The operator controls the process by setting the feedstock rate (How thick the material will be on the rotor) and the rotor heater temperature.

Equipment in Detail

As described in FIG. 7 and FIG. 8, the molecular centrifugal distillation unit receives process cannabinoid or mixture of cannabinoids supplied from a storage tank. This cannabinoid material passes through stainless steel pipes through the variable speed feed pump. This pump controls the flow rate of material through the molecular centrifugal distillation system. From the feed pump the cannabinoid material passes along a length of heated pipe before entering the degasser. Preheated cannabinoid material enters a rotating cup within the degasser and is spun onto the heated walls to quickly out gas the cannabinoid material. The cannabinoid media runs down and is collected on the heated base. Degassed material passes, via a pipeline, to the distillation chamber feed pump.

From the feed pump the cannabinoid material passes along a length of pipe, which is heated to reduce any heat loss, before entering the centrifugal distillation chamber. In the centrifugal distillation chamber the cannabinoid material is introduced onto the center of the spinning rotor disk and is spread across the heated surface. The surface area increases exponentially as cannabinoid material travels across the disc thus exposing more cannabinoid material to the surface for evaporation as it travels across. The cannabinoid material will separate into a vapor phase, the distillate, depending on the operators' combination choice of temperature and pressure. The remaining cannabinoid material is the residue.

The distillate vapor is condensed on a water-cooled surface and flows down the chamber walls and out to the distillate pump. The residue passing across the full surface of the rotor is collected in a surrounding gutter and flows out of the chamber to the residue pump. On the exit of each pump is a non-return valve to isolate the distillation chamber from atmospheric pressure. Both the degasser and distillation chambers have independent vacuum pumping systems which are protected with individual traps.

The traps in each vacuum line are refrigerated to protect from cross-contamination with the vacuum pump fluids. Both traps have drain taps, which are used to empty the traps while the molecular centrifugal distillation unit is shut down and at atmospheric pressure. Trap collection vessels or gear pumps can be added to drain the traps while the molecular distillation unit is running and are supplied as an option. The degasser vacuum pump is a direct drive rotary vane positive displacement pump with exhaust to the atmosphere. The distillation chamber vacuum pumps are a diffusion-ejector pump backed by a direct drive rotary vane positive-displacement pump with exhaust to the atmosphere. System pressures are monitored at the degasser, distillation chamber, and the ejector pump fore line.

FIG. 9 is a flowchart illustrating a non-limiting preferred embodiment of a process of performing a centrifugal distillation followed by performing a cryogenic milling to obtain cannabinoid nanoparticles. FIG. 9 shows a process having the steps: (i) Performing centrifugal distillation of cannabinoid-containing oil, preferably a cannabinoid-containing oil from hemp having less than 0.3% THC, to obtain a cannabis distillate; (ii) Mixing the cannabis distillate with aqueous surfactant and solvent to obtain a cannabinoid emulsion, and homogenizing the cannabinoid emulsion in a homogenizer to obtain a homogenized cannabinoid emulsion; and (iii) Mixing the homogenized cannabinoid emulsion with a cryogenic carrier under pressure to obtain a cryogenic cannabinoid stream, and delivering the cryogenic cannabinoid stream under high speed to a nozzle within a collision chamber to collide the stream with an impact surface to obtain cannabinoid nanoparticles as a powder or slurry.

In a preferred embodiment, the centrifugal distillation to obtain a cannabis distillate is performed using a centrifugal distillation system having a low pressure chamber housing a stationary outer condenser/collector with a rotating inner distiller unit having a rotating heated disk surface, wherein the cannabinoid-containing oil is delivered from a storage tank into the center of the rotating heated disk surface and migrates by centrifugal force as a thin film across the top surface of the rotating heated disk surface towards an adjacent condenser element, wherein first volatile fractions evaporate more rapidly and condense on the condenser unit and are collected, and second/later fractions roll off the rotating heated disk surface and are recirculated into the storage tank for additional centrifugal distillation. Step (ii) comprises mixing the cannabis distillate with aqueous surfactant and solvent to obtain a cannabinoid emulsion, and homogenizing the cannabinoid emulsion in a homogenizer to obtain a homogenized cannabinoid emulsion; and (iii) mixing the homogenized cannabinoid emulsion with a cryogenic carrier under pressure to obtain a cryogenic cannabinoid stream, and delivering the cryogenic cannabinoid stream under high speed to a nozzle within a collision chamber to collide the stream with an impact surface to obtain cannabinoid nanoparticles as a powder.

FIG. 10 is a flowchart illustrating a non-limiting preferred embodiment of a combined process to make cannabinoid nanoparticle powder comprising the steps: (i) Performing centrifugal distillation of cannabinoid-containing oil to obtain a cannabis distillate; (ii) Delivering a homogenized cannabinoid emulsion made from the cannabis distillate mixed under pressure with a cryogenic carrier as a cryogenic cannabinoid stream to a nozzle within a collision chamber to collide the stream(s) with an impact surface and/or with additional stream(s) to obtain cannabinoid nanoparticles as a cannabinoid nanoparticle powder; (iii) Milling the cannabinoid nanoparticle powder and/or sifting the cannabinoid nanoparticle powder through a molecular sieve to obtain a uniform cannabinoid nanoparticle powder having an average particle size of selected from the range of 20-300 nm.

FIG. 11 is a flowchart illustrating a non-limiting preferred embodiment of a combined process to make cannabinoid nanoparticle liposomes comprising the steps of: (i) performing centrifugal distillation of a cannabinoid-containing oil to obtain a cannabis distillate; and then (ii) preparing a homogenized cannabinoid emulsion from the cannabis distillate to mix the emulsion with a cryogenic carrier under pressure to obtain a cryogenic cannabinoid stream, and deliver the cryogenic cannabinoid stream under high speed to a nozzle within a collision chamber to collide the stream with an impact surface to obtain cannabinoid nanoparticles; and finally (iii) formulating the cannabinoid nanoparticles into cannabinoid nanoparticle liposomes.

FIG. 12 is a flowchart illustrating a non-limiting preferred embodiment of a combined process to make cannabinoid nanoparticle liposome powder comprising the steps of: (i) Performing centrifugal distillation of cannabinoid-containing oil to obtain a cannabis distillate; (ii) Delivering a homogenized cannabinoid emulsion made from the cannabis distillate, mixed under pressure with a cryogenic carrier, as a cryogenic cannabinoid stream to a nozzle within a collision chamber to collide one or more of the cryogenic cannabinoid stream(s) with one or more impact surfaces, which may include one or more other cryogenic cannabinoid stream(s), to obtain cannabinoid nanoparticles; (iii) Formulating the cannabinoid nanoparticles into cannabinoid nanoparticle liposomes, and freeze-dry or spray dry the liposomes into a cannabinoid nanoparticle liposome powder; (iv) Milling the cannabinoid nanoparticle liposome powder and/or sifting the cannabinoid nanoparticle liposome powder through a molecular sieve to obtain a uniform cannabinoid nanoparticle liposome powder having an average particle size of selected from the range of 20-300 nm.

FIG. 13 is a chart illustrating cryogenic fluids with their boiling point in Kelvin and degree Celsius.

FIG. 14 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition.

FIG. 15 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition; (iii) mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition.

FIG. 16 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (ii) diluting the aqueous cannabinoid nanoparticle slurry with water 20-480 ml to form a cannabinoid beverage composition; (iii) mixing the cannabinoid beverage composition with a liquid supplement mixture comprising niacinamide (B3) 10-1000 mg, pantothenol (B5) 10-1000 mg, pyridoxine HCl (B6) 1-100 mg, cyanocobalamin (B12) 250-5000 mcg, citicholine 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition; (iv) mixing the cannabinoid beverage composition with a secondary liquid supplement comprising Vitamin C, Vitamin D, Vitamin E, zinc, magnesium, manganese, copper, potassium, and selenium to form an enhanced cannabinoid beverage supplement composition.

FIG. 17 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (b)(ii) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm; (ii) diluting the aqueous cannabinoid nanoparticle slurry with water 20-480 ml to form a cannabinoid beverage composition.

FIG. 18 is a flowchart illustrating a non-limiting preferred embodiment of a process comprising the steps: (i) manufacturing cannabinoid nanoparticles from industrial hemp by (a) Performing centrifugal distillation of cannabinoid-containing oil made from industrial hemp having less than 0.3% THC, to obtain a cannabis distillate; (b) Delivering a homogenized cannabinoid emulsion made from the cannabis distillate mixed under pressure with a cryogenic carrier as at least one cryogenic cannabinoid stream to at least one nozzle within a collision chamber to collide the at least one stream with an impact surface and/or with additional stream(s) to obtain jet milled cannabinoid nanoparticles having an average particle size of 20-300 nm as an aqueous cannabinoid nanoparticle slurry; (b)(ii) Formulating the cannabinoid nanoparticles into cannabinoid nanoparticle liposomes; (ii) diluting the aqueous cannabinoid nanoparticle slurry with water 20-480 ml to form a cannabinoid beverage composition.

Figure 19:
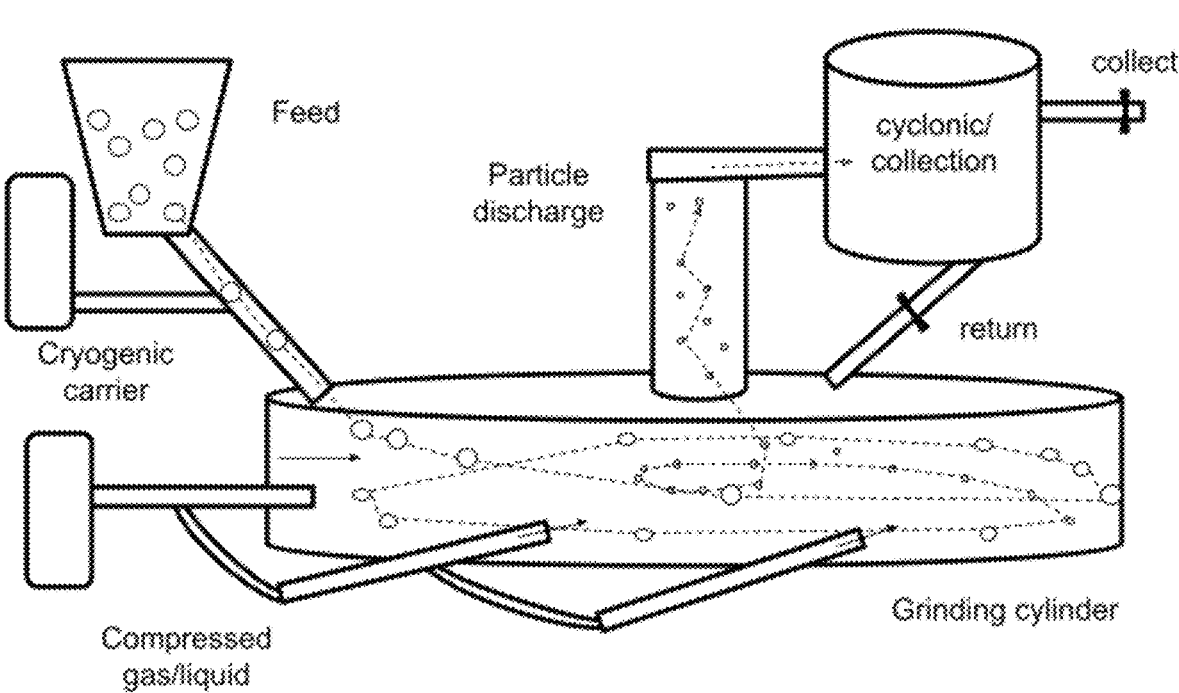
FIG. 19 is an illustration of a basic set up for a jet mill.

FIG. 19 is an illustration of a basic set up for a jet mill. FIG. 19 shows a feed bin with a feed tube delivering a cannabinoid feedstock, e.g. homogenized cannabinoid emulsion, to a jet mill grinding cylinder. The jet mill grinding cylinder is connected to a supply of compressed gas, liquid, or gas/liquid mixture which is delivered to the grinding cylinder. In one preferred embodiment, the compressed gas/liquid is mixed with the cannabinoid feedstock and then delivered to the grinding cylinder as a cryogenic cannabinoid stream. In another preferred embodiment, the feedstock is delivered to the grinding cylinder separately from the compressed gas/liquid. In another embodiment, the cannabinoid feedstock is mixed with the cryogenic carrier and the cryogenic cannabinoid stream is delivered to the grinding cylinder in a feedtube and the compressed gas/liquid, which may the same or different from the cryogenic carrier, is separately delivered to the grinding cylinder via high speed jets.

Pharmaceutical & Nutraceutical Aspects

In some embodiments, the cannabinoid nanoparticle compositions herein, may further contain, in accordance with accepted practices of pharmaceutical compounding, one or more pharmaceutically acceptable excipients, diluents, adjuvants, stabilizers, emulsifiers, preservatives, colorants, buffers, flavor imparting agents. As stated above, the inventive compositions may be consumed directly or formulated into nutraceutical or pharmaceutically acceptable compositions suitable for oral delivery.

Pharmaceutical Compositions/Medicaments

Any of the compositions of the invention may be converted using customary methods into pharmaceutical compositions and medicaments. The pharmaceutical composition and medicaments contain the composition of the invention either alone or together with other active substances. Such pharmaceutical compositions and medicaments can be for oral delivery.

Any of the compositions and medicaments are indicated as therapeutic agents either alone or in conjunction with other therapeutic agents or other forms of treatment. The compositions and agents of the invention are intended for consumption by humans or animals.

Example—Cannabinoid Nanoparticle Oral Formulation

A cannabinoid nanoparticle is prepared, the cannabinoid nanoparticle at a dosage of 0.5-150 mg is homogenized with a dietary oil, an optional secondary solvent and/or surfactant at 0.1-10% w/v, and an optional anti-oxidant. An optional sweetener or flavorant may be added. An oral formulation of cannabinoid nanoparticle is obtained. The dietary oil may comprise medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from ethanol, glycerol, propylene glycol, and polyethylene glycols.

Example—Cannabinoid Nanoparticle Oral Formulation

A cannabinoid nanoparticle is prepared, the cannabinoid nanoparticle at a dosage of 0.5-150 mg is formulated by mixing one or more of a dietary wax, a dietary oil, a solvent and/or surfactant at 0.1-10% w/v, and an optional anti-oxidant. An optional sweetener or flavorant may be added. An oral formulation of cannabinoid nanoparticle is obtained. The dietary wax may comprise beeswax, plant waxes, very long chain fatty acid waxes, and mixtures thereof. The dietary oil may comprise medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from a very long chain fatty alcohol (C24-C34), ethanol, glycerol, propylene glycol, and polyethylene glycols.

Example—Cannabinoid Nanoparticle Oral Formulation

A cannabinoid nanoparticle is prepared, the cannabinoid nanoparticle at a dosage of 0.5-150 mg is formulated by mixing with sesame oil and ethanol. An oral formulation of cannabinoid nanoparticle is obtained.

Example—Cannabinoid Nanoparticle Edible

An edible product comprising a composition of the present invention. Edible products include a cannabinoid nanoparticle formulated in a food composition selected from an edible, a meltable form for adding to hot beverages selected from coffee, tea, cider, cocoa, and mixed hot drinks, a powder or dissolvable form for adding to cold or room temperature beverages selected from a water, a tea, a coffee, a soda/carbonate drink, a cider, a juice, an energy drink, a beer, an ale, a wine, a liquor, and a mixed beverage.

Example—Cannabinoid Nanoparticle Liposomes Oral Formulation

Cannabinoid nanoparticle liposomes are prepared, the cannabinoid nanoparticle liposomes at a dosage of 0.5-150 mg is formulated by mixing one or more of a dietary wax, a dietary oil, a solvent and/or surfactant at 0.1-10% w/v, and an optional anti-oxidant. An optional sweetener or flavorant may be added. An oral formulation of cannabinoid nanoparticle liposomes are obtained. The dietary wax may comprise beeswax, plant waxes, very long chain fatty acid waxes, and mixtures thereof. The dietary oil may comprise medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from a very long chain fatty alcohol (C24-C34), ethanol, glycerol, propylene glycol, and polyethylene glycols.

Dosages

Dosages for cannabinoid nanoparticles or cannabinoid nanoparticle liposomes contemplated as within the scope of the invention include, without limitation, the following dosage examples:

1 mg to 2.5 mg cannabinoid nanoparticles edibles—for mild relief of symptoms like pain, stress, and anxiety; increased focus and creativity.

2.5 mg to 15 mg cannabinoid nanoparticles edibles—for stronger relief of pain and anxiety symptoms; sleep aid.

30 mg to 100 mg cannabinoid nanoparticles edibles—for patients living with inflammatory disorders, cancer, and other serious conditions.

Other preferred dosages of the invention include 1 mg, 2.5 mg, 5 mg, and 10 mg doses. For chemotherapy, as a non-limiting example, a 5 mg capsule is taken 1-3 hours before chemotherapy, and then additional 5 mg doses every 2-4 hours as prescribed or as necessary. For anxiety, appetite increase (e.g. in people diagnosed with AIDS), opioid withdrawal, or narcotic relapse prevention, a patient may take a 1 or 2 mg twice per day, as prescribed.

In another embodiment, the cannabinoid nanoparticles are co-delivered with CBD as a combination delivered simultaneously, or as a combination delivered sequentially. A preferred embodiment includes a ratio of cannabinoid nanoparticles to CBD of about 1:2, or 1:3, or 1:4, or 1:5.

Aqueous Solvent

Any of the present compositions additionally comprise an aqueous solvent. Preferably the aqueous solvent is present in the instant compositions from about 50% to about 95% by weight, and more preferably from about 60% to about 90% by weight.

Preservatives

Any of the presently preferred compositions may optionally further contain at least one preservative. Preferred non-limiting examples of preservatives that can optionally be included in these compositions include benzyl alcohol, methyl paraben, ethyl paraben, derivatives thereof, and mixtures thereof. A particularly preferred preservative in this regard is benzyl alcohol or a derivative thereof. Additionally, the preservative is preferably present in an amount of about 0.1% to about 2.5% by weight of the overall weight of the composition.

Gelling Agents

Any of the presently preferred compositions may optionally further contain a gelling agent. Preferred non-limiting examples of gelling agents that can optionally be included in these compositions include various cellulose agents, such as cellulosic polymers, methylcellulose, hydroxyethylcellulose, hydroxypropylcellulose, and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof. Exemplary polymers which may be useful in the preferred compositions include carboxy vinyl polymers, such as carboxypolymethylene. Additionally preferred gelling agents include Carbopol® and Carbomer® polymers (i.e. polyacrylic polymers) such as is available from Noveon Inc., Cleveland, Ohio. The gelling agent is preferably present in the instant compositions in an amount of from about 0.01% to about 10%, more preferably from about 0.1% to about 5%, and most preferably from about 0.1% to about 2%, by weight.

Anti-Oxidants

Any of the presently preferred compositions may optionally further contain at least one anti-oxidant. Preferably, the presently preferred compositions can comprise about 0.1% to about 5% by weight of at least one anti-oxidant. Preferred non-limiting examples of antioxidants that can optionally be included in these compositions include ascorbic acid, ascorbyl esters of fatty acids, magnesium ascorbyl phosphate, sodium ascorbyl phosphate, ascorbyl sorbate, tocopherol, tocopherol sorbate, tocopherol acetate, butylated hydroxy benzoic acid, thioglycolates, persulfate salts, 6-hydroxy-2,5,7,8-tetramethylchroman-2-carboxylic acid, lipoic acid, gallic acid, propyl gallate, uric acid, sorbic acid, lipoic acid, amines, N,N-diethylhydroxylamine, N-acetyl-L-cysteine, amino-guanidine, sulfhydryl compounds, glutathione, dihydroxy fumaric acid, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, rosemary extracts, derivatives thereof, and mixtures thereof.

Emulsifiers

Any of the presently preferred compositions may optionally further contain an emulsifier. Preferably, the presently preferred compositions can comprise about 0.05% to about 15% by weight, and more preferably from about 0.5% to about 10% by weight of at least one emulsifier. Preferred, non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-8 stearate, PEG-100 stearate, derivatives thereof, and mixtures thereof.

pH Modifiers

Any of the presently preferred compositions may optionally further contain a pH modifier. Preferably, the presently preferred compositions can comprise about 0.001% to about 1% by weight of a pH modifier. Preferred non-limiting examples of neutralizing pH modifiers that can optionally be included in these compositions include inorganic hydroxides, inorganic oxides, inorganic salts of weak acids, derivatives thereof, and mixtures thereof. Preferred, non-limiting examples of inorganic hydroxides useful in this regard include ammonium hydroxide, alkali metal hydroxide, alkaline earth metal hydroxides, derivatives thereof, and mixtures thereof. Preferred inorganic hydroxides useful in this regard include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof. Preferred, non-limiting examples of inorganic oxides useful in this regard include magnesium oxide, calcium oxide, derivatives thereof, and mixtures thereof. Preferred, non-limiting examples of inorganic salts of weak acids useful in this regard include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

Chelating Agents

Any of the presently preferred compositions may optionally further contain a chelating agent. Preferably, the presently preferred compositions can comprise about 0.01% to about 1% by weight of a chelating agent. Preferred non-limiting examples of chelating agents that can optionally be included in these compositions include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and mixtures thereof.

EXAMPLES

The following examples are included to demonstrate embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention. Prophetic examples use present tense verbs for the process steps.

Example 1

Cannabinoid nanoparticle (100 g) powders are prepared using low-frequency sonication drying. The mixture is allowed to freeze overnight and then placed in a funnel connected to a feeder attached to a jet mill. A liquid and gas nitrogen mixture is adjusted resulting in a flow of 100 to 180 CFM (80 to 100 psi combined input pressure) and a temperature of −2 Celsius above the cyclone read from a Flowmeter. The powder is fed into the mill over 5 minutes and the resulting powder in the cup below the cyclone passed again through the mill three additional passes. The resulting white powder in the cup and bag is obtained with a yield of 92 g, containing particles with a diameter less than 10 microns and highly electrostatic. The cannabinoid nanoparticles obtained may be used as a carrier for use in a dry powder inhaler or oral capsule formulation.

Example 2

Spray-dried cannabinoid nanoparticles are mixed with inhalation-grade excipients in a mixer at room temperature for 10 minutes. The resulting dry mix is then granulated in a shear mixer with water. The wet granulation is then spread into a stainless steel bowl and dried. The dried granules are then milled through a mesh (1 mm) screen. The mixture is allowed to freeze overnight and milled similar to the method of EXAMPLE 1. The powder is fed into the mill over 5 minutes and the resulting powder in the cup below the cyclone passed again through the mill three additional passes. The resulting white powder in the bag is obtained with a yield of >60 g, containing particles with a diameter less than 10 microns and highly electrostatic. The particles obtained may be used as an inhaled product.

Example 3

Cannabinoid nanoparticles are mixed with excipients in a mixer at room temperature for 10 minutes. Similar to EXAMPLE 1, the mixture is placed in a funnel connected to a spoon feeder attached to a jet mill. A liquid and gas nitrogen mixture is adjusted resulting in a pressure of 90 psi (+/−10 psi) in each jet. The powder is fed into the mill over approximately 5 minutes and the resulting powder in the cup below the cyclone passed again through the mill for additional passes. The resulting white powder in the bag is obtained with a yield of >60 g, containing particles with a diameter less than 10 microns and highly electrostatic. The particles obtained may be used to fill capsules or added to a heated propylene glycol/aqueous solution in preparation of a clear hydrogel.

Example 4

Cannabinoid nanoparticles are mixed with excipients in a 1 kg batch and milled according to the method described in EXAMPLE 1. Milled cannabinoid nanoparticle formulations demonstrate improved bioavailability in vivo. Oral cannabinoid nanoparticle preparations may be useful in commercial products and medical treatments.

Example 5

Cannabinoid nanoparticles are mixed with excipients in a 1 kg batch and milled according to the method described in EXAMPLE 1. Powders are recovered at >98% each pass and the particle size after each pass has a range 2250 nm-190 nm (Pass 1), 524 nm-44 nm (Pass 2), 400 nm-33 nm (Pass 3), and 264 nm-51 nm (Pass 4). Cannabinoid nanoparticle formulations are developed using milled powder (from Pass 4), with optional.

Example 6

Cannabinoid nanoparticles are mixed with 4% PVP K-30 and milled in 20 kg batches similar to EXAMPLE 1. Cannabinoid nanoparticle powders are recovered at >75% and the particle size was 652 nm 98 nm by Coulter, compared to >3 microns unmilled.

Example 7

Cannabinoid nanoparticles are mixed with 95% methacrylic acid copolymer (Eudragit L100, Rohm) in a 20 kg batch, and dried using a 20% chloroform/80% isopropanol solution in a stainless steel container overnight. Cannabinoid nanoparticles are milled in one or more passes similar to EXAMPLE 1. A white powder is obtained containing Cannabinoid nanoparticles with a diameter from 50 microns and smaller.

Example 8

Cannabinoid nanoparticles having a particle size from 20-40 nm are obtained as described herein and are formulated in an oral taste-masked formulation.

Example 9

Film-Hydration Method

A thin film is created by evaporating a lipid-solvent solution during flask rotation under vacuum. A multi-lamellar vesicle (MLV) suspension can be obtained by adding the aqueous solution to hydrate the lipid film. Particle size can be further reduced to obtain small uni-lamellar vesicles (SUVs), and the drug substance (cannabinoid nanoparticles) can be passively or actively loaded during or after the liposome formation, respectively.

Example 10

50-100 nm Cannabinoid Nanoparticle Liposomes

A cannabinoid nanoparticle liposome is manufactured through evaporating fully hydrogenated soy phosphatidylcholine (HSPC), distearoylphosphatidylglycerol (DSPG), Cholesterol from dichloromethane, hydration with lactose solution, size reduction by homogenization, filtration, and lyophilization, to obtain 50-100 nm cannabinoid nanoparticle liposomes.

Example 11

<100 nm Cannabinoid Nanoparticle Liposomes

A cannabinoid nanoparticle liposome is manufactured through evaporating egg phosphatidylcholine (EPC) and dimyristoylphosphatidylcholine (DMPC) from dichloromethane, hydration with lactose solution, size reduction by homogenization, filtration, and lyophilization, to obtain <100 nm cannabinoid nanoparticle liposomes.

Example 12

50-100 nm Cannabinoid Nanoparticle Liposomes

A cannabinoid nanoparticle liposome is manufactured through evaporating dioleoyl phosphatidylcholine (DOPC) and Cholesterol from dichloromethane, hydration with lactose solution, size reduction by homogenization, filtration, and lyophilization, to obtain 50-100 nm cannabinoid nanoparticle liposomes.

Example 13

100 nm Cannabinoid Nanoparticle Liposomes

A cannabinoid nanoparticle liposome is manufactured through evaporating fully hydrogenated soy phosphatidylcholine (HSPC), N-(carbonyl-methoxy-polyethlyeneglycol-2000)-distearolyphosphatidylethanolamine (MPEG-2000-DSPE) and Cholesterol from dichloromethane, hydration with aqueous solution, size reduction by homogenization, filtration, and lyophilization, to obtain 100 nm cannabinoid nanoparticle liposomes.

Example 14

45-80 nm Cannabinoid Nanoparticle Liposomes

A cannabinoid nanoparticle liposome is manufactured through evaporating distearoyl-phosphatidylcholine (DSPC) and Cholesterol from dichloromethane, hydration with aqueous solution, size reduction by homogenization, filtration, and lyophilization, to obtain 45-80 nm cannabinoid nanoparticle liposomes.

Example 15

110 nm Cannabinoid Nanoparticle Liposomes

A cannabinoid nanoparticle liposome is manufactured through evaporating distearoylphosphatidylcholine (DSPC), N-(carbonyl-methoxy-polyethlyeneglycol-2000)-distearoly-phosphatidylethanolamine (MPEG-2000-DSPE) and Cholesterol from dichloromethane, hydration with aqueous solution, size reduction by homogenization, filtration, and lyophilization, to obtain 110 nm cannabinoid nanoparticle liposomes.

Example 16

Double-Emulsification Method

This technique is used to produce MLVs. The whole production routinely includes four sequential operations as follows: (1) the formation of a "water-in-oil" emulsion, (2) the formation of a "water-in-oil-in-water" emulsion, (3) solvent extraction with the help of stripping gas or vacuum pressure, and (4) microfiltration for the removal of the free drug, concentration, and exchange of external solution.

Example 17

20 nm Cannabinoid Nanoparticle Liposomes

A cannabinoid nanoparticle liposome is manufactured through the double-emulsification method, using dioleoyl phosphatidylcholine (DOPC), dipalmitoylphosphatidylglycerol (DPPG), Cholesterol, and triolein, to obtain 20 nm cannabinoid nanoparticle MLV liposomes.

Example 18

24-31 nm Cannabinoid Nanoparticle Liposomes

A cannabinoid nanoparticle liposome is manufactured through the double-emulsification method, using dierucoyl phosphatidylcholine (DEPC), dipalmitoylphosphatidylglycerol (DPPG), Cholesterol, and tricaprylin, to obtain 24-31 nm cannabinoid nanoparticle MLV liposomes.

Example 19

17-23 nm Cannabinoid Nanoparticle Liposomes

A cannabinoid nanoparticle liposome is manufactured through the double-emulsification method, using dioleoyl phosphatidylcholine (DOPC), dipalmitoylphosphatidylglycerol (DPPG), Cholesterol, triolein, and tricaprylin to obtain 17-23 nm cannabinoid nanoparticle MLV liposomes.

Example 20

Solvent Injection Technique

Solvent Injection Technique dissolves lipid materials and lipophilic substances in a water-miscible organic solvent, and then the organic phase is injected into a large amount of aqueous buffer, resulting in unilamellar vesicle liposomes (Small UVs, Large UVs) being spontaneously formed. In another method, two streams of solution are injected/infused through the Y-connector and membrane contactors in a tubular device to improve the micromixing of the organic phase into the aqueous phase. The solvent rapidly diffuses in an aqueous medium, and interfacial turbulence leads to the formation of small and homogenous liposomes. The particle size between 80 nm and 300 nm is prepared depending on the preparation conditions. Additional energy input for particle size reduction, such as sonication and extrusion, is not required. The organic solvent is removed using evaporation, lyophilization, dialysis, or diafiltration, and the liposomes suspensions may be concentrated to a desired volume. Ethanol is commonly used as an organic solvent because of its safety. Various preparation parameters, including the flow rate, the temperature of both solvent and aqueous solution, the lipid concentration, as well as the stirring rate, affect the properties of particles.

Example 21

200-300 nm Cannabinoid Nanoparticle Liposomes

A cannabinoid nanoparticle liposome is manufactured through the double-emulsification method, using dipalmitoyl phosphatidylcholine (DPPC), and Cholesterol, and an ethanol infusion to minimize the amount of lipids-ethanol solution and the cannabinoid nanoparticles are mixed by a Y-connector and in-line mixer to form 200-300 nm cannabinoid nanoparticle liposomes.

Nano-Encapsulation

Accordingly, the invention provides a simplified method of nanoencapsulation wherein the capsule shell consists of a lipid composition that encapsulates high purity cannabinoid nanoparticles or mixture of high purity cannabinoid nanoparticles that maintain the size of said cannabinoid nanoparticles. The invention provides a simplified method of encapsulating cannabinoids that have been highly purified via molecular distillation prior to a wide variety of mixing or homogenization or sonication or high shear blending resulting in cannabinoid nanoparticles of the highest stability and purity. The invention provides a nano-suspension of encapsulated cannabinoid product having an infusible polymer shell. The invention provides a nano-suspension of encapsulated cannabinoid product wherein the product is readily dispersed or suspended into an aqueous solution. The invention provides a nano-suspension of encapsulated cannabinoid product having high uniformity of thickness of the polymeric capsule shell. The invention provides a dry, free-flowing, discrete nanoscopic cannabinoid capsule in said cannabinoid nano-suspension.

The invention provides a sequence that obtains cannabinoid nanoparticles or mixture of cannabinoid nanoparticles from unpurified raw cannabinoid oil to a purified cannabinoid resulting from the extraction or purification using a molecular distillation process that forms a high purity cannabinoid prior to its nano-suspension into an aqueous or non-aqueous media nanoencapsulation. Essentially, the process comprises bringing a cannabinoid or mixture of cannabinoids together with a lipid or lipophilic substance that when mixed together in the proper sequence produces cannabinoid nanoparticles of size ranging from 50 to 1000 nm and preferably 100 to 500 nm in size.

Example 22

A cannabinoid nanoparticle powder or cannabinoid nanoparticle liposome is mixed with an aqueous encapsulant such as sodium alginate, agarose, gelatin, or pectin, and then stirred with a cross-linking agent such as calcium chloride. The encapsulated cannabinoid nanoparticle is cold-pressed, dried, and the dried material is milled to an encapsulated cannabinoid nanoparticle powder. The cannabinoid nanoparticle may be completely released from encapsulation by dissolving in a buffered solution.

Example 23

A cannabinoid nanoparticle powder or cannabinoid nanoparticle liposome is mixed with an aqueous encapsulant such as lactose, then freeze-dried, and the dried material is milled to an encapsulated cannabinoid nanoparticle powder. The cannabinoid nanoparticle may be completely released from encapsulation by dissolving in a buffered solution.

Example 24

Nano-Emulsions

The invention provides, at the reaction interface where condensation of the cannabinoid occurs said cannabinoid composition substantially and instantaneously forms a thin film of cannabinoid or mixture of cannabinoids which is insoluble in the parent media of the lipid composition that will result in the formation of the cannabinoid or mixture of cannabinoid nanoparticles. The preferred and mechanically most simple method of providing the interface for nano-suspension is to disperse or emulsify one cannabinoid or a mixture of cannabinoids for the condensation polymer in a continuous phase containing the second reactant. The cannabinoid substance to be processed into a cannabinoid nano-encapsulation will also be contained in the dispersed phase. However, in order to more accurately control the formation of the nano-suspension, it can be convenient to emulsify or disperse one cannabinoid or mixture of cannabinoids for the condensation polymer, together with the substance to be nano-suspended in a continuous phase and thereafter add additional continuous phase containing the second reactant to the dispersion. The polycondensation polymer shell will form at the interface of the dispersed cannabinoid composition and encapsulate the material resulting in a cannabinoid nano-suspension. The suspension or nanoparticle. The dispersion or emulsion can be stabilized by addition of surface active agents, or surfactants, or co-surfactants or protective colloids to the continuous phase. The dispersion or emulsion can be produced by the standard suspension and emulsification techniques known in the art. Emulsions or dispersions can be prepared by agitation, preferably in the presence of one or more emulsifying agents. The efficiency of the emulsification depends among other factors, on the type and degree of agitation and the manner in which the emulsifying agent is introduced. The primary function of the agitation is to break up both phases of the emulsion so that the one which will become the dispersed phase is able to form small globules. The emulsifier is employed to lower the interfacial tension since the lower the interfacial tension the lower the amount of mechanical energy needed to break up the phases. Where the interfacial tension of a system is extremely low, spontaneous emulsification may result. The preparation of the emulsions can be facilitated by various types of colloid mills and homogenizers engineered to obtain maximum shear action of the fluid and enhance the formation of fine uniform globules. The use of such emulsifier will result in a more stable cannabinoid nano-suspension and can also result in a more effective cannabinoid nano-suspension which can deliver greater therapeutic effects.

Emulsifying agents which are operable in preparing the emulsions or dispersions or suspensions that will be used to produce the cannabinoid or mixture of cannabinoid nanoparticles include the long chain polar and non-polar compounds, as well as the more complex hydrophilic colloids, such as gums, starches, proteins, etc. which are known to be readily adsorbed at the phase interfaces. In addition to high shear agitation with or without emulsifier, the nano-suspension dispersion can be formed by injecting one phase into a second phase from an orifice at a rate designed to exceed the critical velocity required for continuous flow. A solid phase containing one cannabinoid or mixture of cannabinoids may be dispersed into a continuous medium containing the second reactant. The continuous medium may contain the second reactant or a solution of the second reactant also as a discontinuous phase. Such would be the case when a liquid or solid medium containing the first cannabinoid or mixture of cannabinoids is dispersed into a continuous phase containing a fine dispersion of the second reactant resulting in a more effective cannabinoid nano-suspension. The effective reactive area of the second reactant can be increased by reducing the particle size of its dispersion and thus resulting in the formation of cannabinoid or mixture of cannabinoid nanoparticles.

EQUIVALENTS

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

What is claimed:

1. A cannabinoid beverage composition, comprising: (i) water; (ii) cannabinoid nanoparticles 1-30 mg with at least one dimension less than 100 nm; and (iii) a mixture of niacinamide (vitamin B3) 10-1000 mg, pantothenol (vitamin B5) 10-1000 mg, pyridoxine HCl (vitamin B6) 1-100 mg, cyanocobalamin (vitamin B12) 250-5000 mcg, citicoline 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg.

2. The cannabinoid beverage composition according to claim 1, further comprising: vitamin C, vitamin D, vitamin E, zinc, magnesium, manganese, copper, potassium, selenium.

3. A cannabinoid beverage composition, comprising: (i) water 44-60 ml; (ii) cannabinoid nanoparticles 1-30 mg with at least one dimension less than 100 nm; (iii) a mixture of niacinamide (vitamin B3) 40 mg, pyridoxine HCl (vitamin B6) 40 mg, cyanocobalamin (vitamin B12) 500 mcg, citicoline 10-1000 mg, a 60:40 blend of L-phenylalanine:N-acetyl-L-4-hydroxyphenylalanine 250-1000 mg, taurine 10-3000 mg, malic acid, glucuronolactone 100-1000 mg, and caffeine 60-250 mg.

4. The cannabinoid beverage composition according to claim 1, wherein the cannabinoid nanoparticles are an aqueous slurry.

5. The cannabinoid beverage composition according to claim 1, wherein the cannabinoid nanoparticles are a powder having a surfactant coating.

6. The cannabinoid beverage composition according to claim 1, wherein the cannabinoid nanoparticles with at least one dimension less than 50 nm.

7. The cannabinoid beverage composition according to claim 1, wherein the water is 20-480 ml.

8. The cannabinoid beverage composition according to claim 1, wherein the water is 44-60 ml.

9. The cannabinoid beverage composition according to claim 1, wherein the cannabinoid nanoparticles are a nano-suspension of a cannabinoid nanoparticle powder having a surfactant coating.

10. The cannabinoid beverage composition according to claim 1, wherein the cannabinoid nanoparticles are with at least one dimension less than 50 nm.

11. A process for manufacturing a cannabinoid beverage composition from cannabinoid nanoparticles made from industrial hemp, comprising the steps: (i) performing centrifugal distillation of cannabinoid-containing oil made from industrial hemp having less than 0.3% THC, to obtain a *cannabis* distillate; (ii) preparing Preparing a homogenized cannabinoid emulsion from the *cannabis* distillate mixed with aqueous surfactant and solvent, and delivering the homogenized cannabinoid emulsion under pressure with a cryogenic carrier fluid as a cryogenic cannabinoid stream to at least one nozzle within a collision chamber to collide the cryogenic cannabinoid stream with an impact surface and/or with one or more additional stream(s) to obtain jet milled cannabinoid nanoparticles having an average particle size of 20-300 nm as an aqueous cannabinoid nanoparticle slurry; (iii) diluting the aqueous cannabinoid nanoparticle slurry with water 20-480 ml to form a cannabinoid beverage composition; (iv) mixing the cannabinoid beverage composition with a liquid supplement mixture comprising niacinamide (vitamin B3) 10-1000 mg, pantothenol (vitamin B5) 10-1000 mg, pyridoxine HCl (vitamin B6) 1-100 mg, cyanocobalamin (vitamin B12) 250-5000 mcg, citicoline 500-4000 mg, a 60:40 blend of L-phenylalanine:N-acetyl-L-4-hydroxyphenylalanine 250-1000 mg, taurine 40-3000 mg, malic acid, glucuronolactone 400-800 mg, and caffeine 60-300 mg to form a cannabinoid beverage supplement composition; and (v) optionally mixing the cannabinoid beverage composition with a secondary liquid supplement comprising vitamin C, vitamin D, vitamin E, zinc, magnesium, manganese, copper, potassium, and selenium to form an enhanced cannabinoid beverage supplement composition.

12. The process according to claim 11, further comprising the step of: (ii)(b) drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size of selected from the range of 20-300 nm.

13. The process according to claim 11, further comprising the step: (ii)(b) formulating the cannabinoid nanoparticles into cannabinoid nanoparticle liposomes.

14. The process according to claim 12, further comprising the step: drying and milling the jet milled cannabinoid nanoparticles into a cannabinoid nanoparticle powder and optionally sifting the cannabinoid nanoparticle powder through a molecular sieve to obtain a uniform cannabinoid nanoparticle powder having an average particle size less than 100 nm.

15. The process according to claim 11, comprising the step wherein the cannabinoid nanoparticles are formulated as a nanosuspension or as a nanoemulsion.

16. The process according to claim 11, wherein the cannabinoid nanoparticles are dried using low-frequency sonication drying, the dried cannabinoid nanoparticles mixture is allowed to freeze overnight and then placed in a funnel connected to a feeder attached to a jet mill, the cryogenic carrier fluid is a liquid and gas nitrogen mixture adjusted to a flow of 100 to 180 CFM, 80 to 100 psi, combined input pressure and a temperature of −2° C. above a cyclone read from a flowmeter, the dried cannabinoid nanoparticles mixture is fed into the jet mill over 5 minutes and the resulting powder in a jet mill cup below a jet mill cyclone is passed again through the mill three additional passes, the resulting jet-milled dried cannabinoid nanoparticles powder having a diameter less than 10 microns.

17. The process according to claim 11, wherein the cannabinoid nanoparticles are spray-dried cannabinoid nanoparticles mixed with inhalation-grade excipients in a mixer at room temperature for 10 minutes, the resulting dry mix is then granulated in a shear mixer with water, the wet granulation is then spread into a stainless steel bowl and dried, the dried granules are then milled through a 1 mm mesh screen, the mixture is allowed to freeze overnight and jet milled over 5 minutes and the resulting powder in the cup below the cyclone passed again through the mill three additional passes, the resulting jet-milled dried cannabinoid nanoparticles powder having a diameter less than 10 microns.

18. The process according to claim 11, wherein the cannabinoid nanoparticles are mixed with excipients in a mixer at room temperature for 10 minutes, the mixture is placed in a funnel connected to a spoon feeder attached to a jet mill, the jet mill liquid and gas nitrogen mixture is adjusted resulting in a pressure of 90 psi+/−10 psi in each jet, the powder is fed into the mill over approximately 5 minutes and the resulting powder in the cup below the cyclone passed again through the mill for additional passes, the resulting jet-milled dried cannabinoid nanoparticles powder having a diameter less than 10 microns, and the particles optionally added to a heated propylene glycol/aqueous solution in preparation of a clear hydrogel.

19. The process according to claim 11, wherein the cannabinoid nanoparticles are mixed with excipients in a 1 kg batch and jet milled.

20. The process according to claim 11, wherein the cannabinoid nanoparticles are mixed with excipients in a 1 kg batch and jet milled, the powders are recovered at >98% each pass and the particle size after each pass has a range 190-2250 nm Pass 1, 44-524 nm Pass 2, 33-400 nm Pass 3, and 51-264 nm Pass 4, the cannabinoid nanoparticle formulations are developed using milled powder from Pass 4.

21. The process according to claim 11, wherein the cannabinoid nanoparticles are mixed with 4% PVP K-30 and jet milled in 20 kg batches, the cannabinoid nanoparticle powders are recovered at >75% and the particle size ranges from 98-652 nm.

22. The process according to claim 11, wherein the cannabinoid nanoparticles are mixed with 95% methacrylic acid copolymer in a 20 kg batch, and dried using a 20% chloroform/80% isopropanol solution in a stainless steel container overnight, the cannabinoid nanoparticles are jet milled in one or more passes, the cannabinoid nanoparticles with a diameter from 50 microns and smaller.

23. The process according to claim 11, wherein the cannabinoid nanoparticles are formulated in an oral taste-masked formulation.

24. The process according to claim 11, wherein the cannabinoid nanoparticles are loaded into liposomes to produce a cannabinoid nanoparticle liposome product.

25. The process according to claim 24, wherein the cannabinoid nanoparticle liposome is selected from one of the following: a 50-100 nm cannabinoid nanoparticle liposome product manufactured through evaporating fully hydrogenated soy phosphatidylcholine (HSPC), distearoylphosphatidylglycerol (DSPG), cholesterol from dichloromethane, hydration with lactose solution, size reduction by homogenization, filtration, and lyophilization; a <100 nm cannabinoid nanoparticle liposome product manufactured through evaporating egg phosphatidylcholine (EPC) and dimyristoylphosphatidylcholine (DMPC) from dichloromethane, hydration with lactose solution, size reduction by homogenization, filtration, and lyophilization; a 50-100 nm cannabinoid nanoparticle liposome product manufactured through evaporating dioleoyl phosphatidylcholine (DOPC) and cholesterol from dichloromethane, hydration with lactose solution, size reduction by homogenization, filtration, and lyophilization; a 100 nm cannabinoid nanoparticle liposome product manufactured through evaporating fully hydrogenated soy phosphatidylcholine (HSPC), N-(carbonyl-methoxy-polyethlyeneglycol-2000)-distearolyphosphatidylethanolamine (MPEG-2000-DSPE) and cholesterol from dichloromethane, hydration with aqueous solution, size reduction by homogenization, filtration, and lyophilization; a 45-80 nm cannabinoid nanoparticle liposome product manufactured through evaporating distearoyl-phosphatidylcholine (DSPC) and cholesterol from dichloromethane, hydration with aqueous solution, size reduction by homogenization, filtration, and lyophilization; and a 110 nm cannabinoid nanoparticle liposome product manufactured through evaporating distearoylphosphatidylcholine (DSPC), N-(carbonyl-methoxy-polyethlyeneglycol-2000)-distearolyphosphatidylethanolamine (MPEG-2000-DSPE) and cholesterol from dichloromethane, hydration with aqueous solution, size reduction by homogenization, filtration, and lyophilization.

26. The process according to claim 24, wherein the cannabinoid nanoparticle liposome is selected from one of the following: a 20 nm cannabinoid nanoparticle liposome product manufactured through a double-emulsification method, using dioleoyl phosphatidylcholine (DOPC), dipalmitoylphosphatidylglycerol (DPPG), cholesterol, and triolein, to obtain 20 nm cannabinoid nanoparticle multi lamellar vesicle (MLV) liposomes; a 24-31 nm cannabinoid nanoparticle liposome product manufactured through a double-emulsification method, using dierucoyl phosphatidylcholine (DEPC), dipalmitoylphosphatidylglycerol (DPPG), cholesterol, and tricaprylin, to obtain 24-31 nm cannabinoid nanoparticle MLV liposomes; and a 17-23 nm cannabinoid nanoparticle liposome product manufactured through a double-emulsification method, using dioleoyl phosphatidylcholine (DOPC), dipalmitoylphosphatidylglycerol (DPPG), cholesterol, triolein, and tricaprylin to obtain 17-23 nm cannabinoid nanoparticle MLV liposomes.

27. The process according to claim 24, wherein the cannabinoid nanoparticle liposome is selected from one of the following: a 200-300 nm cannabinoid nanoparticle liposome product manufactured through a double-emulsification method, using dipalmitoyl phosphatidylcholine (DPPC), and cholesterol, and an ethanol infusion to minimize the amount of lipids-ethanol solution and the cannabinoid nanoparticles are mixed by a Y-connector and in-line mixer to form 200-300 nm cannabinoid nanoparticle liposomes.

28. The process according to claim 24, wherein the cannabinoid nanoparticle is encapsulated in an infusible polymer shell to obtain a dry, free flowing encapsulated cannabinoid product having high uniformity of thickness, the infusible polymer shell comprising an aqueous encapsulant selected from lactose, sodium alginate, agarose, gelatin, or pectin, the encapsulated cannabinoid nanoparticle is cold-pressed, dried, and the dried material is milled to an encapsulated cannabinoid nanoparticle powder.

29. The process according to claim 24, wherein the cannabinoid nanoparticle is formulated with an emulsifier as a nano-emulsion.

* * * * *